(12) United States Patent
Madou et al.

(10) Patent No.: US 6,663,615 B1
(45) Date of Patent: Dec. 16, 2003

(54) DUAL STAGE MICROVALVE AND METHOD OF USE

(75) Inventors: Marc J. Madou, San Diego, CA (US); Sylvia Daunert, Lexington, KY (US)

(73) Assignees: The Ohio State University, Columbus, OH (US); University of Kentucky, Lexington, KY (US)

( * ) Notice: Subject to any disclaimer, the term of this patent is extended or adjusted under 35 U.S.C. 154(b) by 169 days.

(21) Appl. No.: 09/946,790

(22) Filed: Sep. 4, 2001

(51) Int. Cl.[7] .................... A61K 9/22; A61M 31/00; A61B 5/05

(52) U.S. Cl. .................. 604/891.1; 604/66; 600/345; 600/365

(58) Field of Search .................. 604/890.1, 891.1, 604/892.1, 65, 66, 131; 600/309, 345, 347, 348, 365

(56) References Cited

U.S. PATENT DOCUMENTS

| | | | |
|---|---|---|---|
| 4,765,864 A | 8/1988 | Holland et al. | 156/644 |
| 4,874,500 A | 10/1989 | Madou et al. | 204/412 |
| 4,909,908 A | 3/1990 | Ross et al. | 204/1 T |
| 5,170,801 A | 12/1992 | Casper et al. | 128/769 |
| 5,183,549 A | 2/1993 | Joseph et al. | 204/415 |
| 5,304,293 A | 4/1994 | Tierney et al. | 204/414 |
| 5,337,747 A * | 8/1994 | Neftel | 600/347 |
| 5,366,454 A | 11/1994 | Currie et al. | 604/890.1 |
| 5,368,704 A | 11/1994 | Madou et al. | 205/665 |
| 5,403,680 A | 4/1995 | Otagawa et al. | 429/213 |
| 5,634,899 A | 6/1997 | Shapland et al. | 604/51 |
| 5,660,680 A | 8/1997 | Keller | 438/50 |
| 5,755,408 A | 5/1998 | Schmidt et al. | 244/204 |
| 5,797,898 A | 8/1998 | Santini, Jr. et al. | 604/890.1 |
| 5,877,580 A | 3/1999 | Swierkowski | 310/328 |
| 5,954,685 A | 9/1999 | Tierney | 604/20 |

(List continued on next page.)

OTHER PUBLICATIONS

Shokji, S. and M. Esashi, "Microflow Devices and Systems," J. Micromech. Microeng., 4: 157–71 (1994).*

Santini, Jr., J.T., M. J. Cima, and R. Langer, "A Controlled–Release Microchip," Nature, 397: 335–38 (1999).*

Santini, Jr., J.T., A.C. Richards, R. Scheidt, M. J. Cima, and R. Langer, "Microchips as Controlled Drug–Delivery Devices," Angew. Chem. Int. Ed. 39: 2396–407 (2000).*

Badesch, D.E.A., *Continuous intravenous epoprostenol for pulmonary hypertension due to the scleroderma spectrum of disease.* Ann. Intern. Med., 2000. 132(6): p. 425–434.

Hooper, M.M., M.D., et al., *A comparison of the acute hemodynamic effects of inhaled nitric oxide and aerosolized iloprost in primary pulmonary hypertension.* American College of Cardiology, 2000. 35(1): p. 176–182.

(List continued on next page.)

*Primary Examiner*—Manuel Mendez
*Assistant Examiner*—Mark K Han
(74) *Attorney, Agent, or Firm*—Standley & Gilcrest

(57) ABSTRACT

A micro-machined drug delivery device and method of use for the delivery of labile drugs is disclosed. A micro-machined sensing device and method of use is also disclosed. A micro-machined drug delivery and sensing device and method of use is additionally disclosed. All three devices are intended to be inserted into a patient's body. The drug delivery devices allow for the mixing of drug components prior to the release of the mixture into the patient's body where the mixture is labile. The micro-machined sensing device is suitable for monitoring the concentration of a specific chemical in a patient's body fluids when the monitoring requires a labile reagent that must be mixed prior to introduction of the body fluid into the sensing device. The micro-machined drug delivery and sensing device is especially applicable in situations where the prompt delivery of labile drugs is necessary.

23 Claims, 30 Drawing Sheets

U.S. PATENT DOCUMENTS

| | | | | |
|---|---|---|---|---|
| 5,962,081 | A | 10/1999 | Ohman et al. | 427/534 |
| 5,976,109 | A | 11/1999 | Heruth | 604/140 |
| 5,985,328 | A | 11/1999 | Chu et al. | 424/489 |
| 5,989,445 | A | 11/1999 | Wise et al. | 216/62 |
| 5,993,414 | A | 11/1999 | Haller | 604/93 |
| 6,010,492 | A | 1/2000 | Jacobsen et al. | 604/503 |
| 6,056,734 | A | 5/2000 | Jacobsen et al. | 604/891.1 |
| 6,123,861 | A | 9/2000 | Santini, Jr. et al. | 216/2 |
| 6,136,212 | A | 10/2000 | Mastrangelo et al. | 216/49 |
| 6,181,963 | B1 | 1/2001 | Chin et al. | 604/20 |
| 6,206,914 | B1 | 3/2001 | Soykan et al. | 623/1.42 |
| 6,240,312 | B1 | 5/2001 | Alfano et al. | 600/476 |
| 6,240,317 | B1 | 5/2001 | Villaseca et al. | 607/60 |
| 6,405,066 | B1 * | 6/2002 | Essenpreis et al. | 600/347 |
| 6,491,666 | B1 * | 12/2002 | Santini, Jr. et al. | 604/890.1 |

OTHER PUBLICATIONS

Ensor, C.M., et al., Cloning and sequence analysis of the cDNA for human placental NAD(+)–dependent 15–hydroxyprostaglandin dehydrogenase. J. Biol. Chem., 1990. 265(25): p. 14888–91.

Ensor, C.M. and H.H. Tai, *Bacterial expression and site–directed mutagenesis of two critical residues (tyrosine–151 and lysine–155) of human placental NAD(+)–dependent 15–hydroxyprostaglandin dehydrogenase.* Biochim. Biophys. Acta, 1994. 1208(1): p. 151–6.

Ensor, C.M., H. Zhang, and H.H. Tai, *Purification, cDNA cloning and expression of 15–oxoprostaglandin 13–reductase from pig lung.* Biochem. J., 1998. 330(Pt 1): p. 103–8.

*Drug delivery showing strength in wake of drug efficacy efforts.* Chemical Market Reporter, 1997. 252 (Sep. ): p. 10.

*Drug delivery system: polymers expected to dominate world market by 1996.* Gazeta Mercantil.

Wilson, G. and Y. Hu, Enzyme–based biosensors for in vivo measurements. Chem. Rev., 2000. 100(7): p. 2693–2704.

Madou, M.J. and M. Tierney. 1994: *Micro–electrochemical valves and methods,* United States Patent, 5,368,704.

Glaxo Wellcome, I., www.glaxowellcome.com.

Wilson, G. and Y. Hu, Enzyme–based biosensors for in vivo measurements. Chem. Rev., 2000. 100(7): p. 2693–2704.

Bowyer, J.R., et al., Energy Res. Abstr., 1991: p. 30.

Xie, S.L., E. Wilkins, and P. Atanasov, Sens. Actuators, 1994. 17(2): p. 133–42.

Madou, M.J. and M. Tierney. 1994: *Micro–electrochemical valves and methods,* United States Patent, 5,368,704.

Glaxo Wellcome, I., www.glaxowellcome.com.

*United Therapeutics Corporation S–1 filing.* Securities and Exchange Commission: EDGAR, 1999 (Apr.).

Badesch, D.E.A., *Continuous intravenous epoprostenol for pulmonary hypertension due to the scleroderma spectrum of disease.* Ann. Intern. Med., 2000. 132(6): p.425–434.

Dollery, C.T., *Ther. Drugs.* 1998.

Hooper, M.M., M.D., et al., *A comparison of the acute hemodynamic effects of inhaled nitric oxide and aerosolized iloprost in primary pulmonary hypertension.* American College of Cardiology, 2000. 35(1): p. 176–182.

Ensor, C.M., et al., *Cloning and sequence analysis of the cDNA for human placental NAD(+)–dependent 15–hydroxyprostaglandin dehydrogenase.* J. Biol. Chem., 1990. 265(25): p. 14888–91.

Ensor, C.M. and H.H. Tai, *Bacterial expression and site–directed mutagenesis of two critical residues (tyrosine–151 and lysine–155) of human placental NAD(+)–dependent 15–hydroxyprostaglandin dehydrogenase.* Biochim. Biophys. Acta, 1994. 1208(1): p. 151–6.

Ensor, C.M., H. Zhang, and H.H. Tai, *Purification, cDNA cloning and expression of 15–oxoprostaglandin 13–reductase from pig lung.* Biochem. J., 1998. 330(Pt 1): p. 103–8.

*Drug delivery showing strength in wake of drug efficacy efforts.* Chemical Market Reporter, 1997. 252 (Sep. ): p. 10.

*Drug delivery deveopment proliferation.* Medical & Healthcare Marketplace Guide, 1997 (Jan.).

*Drug delivery market faces increased consolidation.* Chemical Market Reporter, 1998 (Nov.).

*Drug delivery systems:* polymers expected dominate world market by 1996. Gazeta Mercantil.

*Drug delivery changing times.* Med. Ad. News, 1999. 18 (Aug.): p. 8.

* cited by examiner

DUAL STAGE MICROVALVE AND METHOD OF USE

TECHNICAL FIELD OF THE INVENTION

This invention relates to micro-machined drug delivery devices and sensors. Specifically, this invention relates to controlled time and rate release multi-staged drug delivery devices and sensors that employ labile drugs, chemicals and molecules.

BACKGROUND OF THE INVENTION

The delivery of drugs is an important aspect of medical treatment. The efficacy of many drugs is directly related to the way in which they are administered. Some therapies require that the drug be repeatedly administered to the patient over a long period of time. This makes the selection of a proper drug delivery method problematic. Patients often forget, are unwilling or are unable to take their medication. Drug delivery also becomes problematic when the drugs are too potent for systemic delivery. Therefore, attempts have been made to design and fabricate a delivery device that is capable of the controlled, pulsatile or continuous release of a wide variety of molecules including, but not limited to, drugs and other therapies.

U.S. Pat. No. 5,797,898 to Santini, Jr. et al. discloses a microchip drug delivery device that consists of a substrate in which at least two reservoirs are formed. Drugs are deposited into the reservoirs. The drugs are kept in the reservoirs by reservoir caps. The drugs are released into the patient by either diffusion through the reservoir cap or by disintegration of the reservoir cap.

The Santini, Jr. et al. device is suitable for delivery of drugs with a lengthy shelf life, however, many drugs are labile. The labile drugs may undergo changes when mixed with pharmaceutical carriers, buffer, or other drugs thus reducing their potency. Additionally, some drugs have such short-lived effective lives that they must be formed almost immediately prior to administration of the drug to the patient. These drugs are not suitable for use in the device taught by Santini, Jr. et al. because the device provides for a singular reservoir. That is to say, the Santini reference does not teach a drug delivery device wherein active components may be separately stored and mixed prior to being released from the delivery device.

Additionally, there is a need for an in vivo biosensing system that can be implanted in a patient and which uses labile sensing reagents. In many cases, desirable sensing reagents are labile and their use results in short-lived sensing systems. A method that would allow for their use over extended periods of time would broaden current in vitro as well as in vivo sensing options considerably. One approach that has been proposed to overcome the problem surrounding the use of labile reagents in in vivo biosensing systems involves the infusion of fresh reagents through an external septum located at the interface of the skin and the subcutaneous tissue [Wilson, G. and Yu. Hu 2000; Bowyer J. R. 1991; Xie, S. L. 1994]. Unfortunately, the drawback of this method is the possible onset of sepsis in the patient's body.

It is therefore an object of the present invention to provide a micro-machined drug delivery device suitable for the delivery of labile drugs, which can operate for weeks or years at a time. It is another object of the present invention to provide a device that allows for the delivery of drugs, molecules or chemicals to a patient in either a pulsitile or continuous manner. It is yet another object of the present invention to provide a device that allows for two or more drugs, chemicals or molecules that have been separately stored in the device to be mixed before being released from the device into the patient. It is yet another object of the present invention to provide a device whose delivery of drugs, chemicals, or molecules to a patient can be controlled either passively or actively. It is also an object of the present invention to provide a device small enough to be implanted in a patient that can hold many different drugs, chemicals, or molecules. It is also an object of the present invention to provide a biosensing device that uses labile reagents and can be implanted into a patient.

SUMMARY OF THE INVENTION

The present invention presents a novel approach for the delivery of a wide variety of drugs by a micro-machined delivery device. The present invention also presents a novel approach for biosensing using labile reagents. Additionally, the present invention presents a novel micro-machined drug delivery and sensor device. Micro-machined devices are constructed using methods commonly applied to the manufacture of integrated circuits such as ultraviolet (UV) photolithography, reactive ion etching, electron beam evaporation, vapor deposition and spin casting.

A micro-machined drug delivery device for the release of molecules of the present invention comprises a substrate with at least one reservoir. Each reservoir has a first stage and a second stage each containing molecules. Further, each reservoir has a reservoir cap positioned on the reservoir over the molecules in the second stage. Each reservoir has a reservoir partition that separates the first stage from the second stage.

A micro-machined biosensing device for the measuring of the concentration of a chemical in the body fluid of a patient of the present invention comprises a substrate with at least one reservoir in the substrate. Each reservoir has a first stage containing a first type of molecules and a second stage containing a second type of molecules. A pair of sensing electrodes is disposed in the second stage of the reservoir. A reservoir cap is positioned on each reservoir over the molecules in the second stage. A reservoir partition separates the first stage from the second stage.

A micro-machined drug delivery and biosensing device, for sensing a concentration of a chemical in a patient and administering drugs of the present invention comprises a substrate in which at least one drug delivery reservoir is disposed and in which at least one sensing reservoir is disposed. Each drug delivery reservoir and each sensing reservoir has a first stage containing molecules and a second stage containing molecules. Each drug delivery reservoir and each sensing reservoir further has a reservoir partition positioned between and separating the first stage and the second stage. Each drug delivery reservoir and each sensing reservoir has a reservoir cap positioned over the molecules in the second stage. The second stage of each sensing reservoir has a pair of sensing electrodes.

A method for releasing molecules in a patient of the present invention comprises inserting a micro-machined drug delivery device in a patient, contacting the molecules in the first stage with molecules in the second stage so as to form a mixture and releasing the mixture from the micro-machined drug delivery system.

A method for sensing a concentration of a chemical in a patient's body fluids of the present invention comprises inserting a micro-machined sensing device into said patient, contacting molecules in the first stage of the micro-machined device with molecules in the second stage so as to form a sensing element by disintegrating a reservoir partition thereby combining the first stage and second stage to form a volume, permitting body fluid to enter the volume where the body fluid reacts with the recently formed sensing element to produce a signal detected by sensing electrodes, and sending said detected signal to control circuitry.

A method for sensing a concentration of a chemical in a patient's body fluids and releasing drugs into the patient's body of the present invention comprises inserting a micro-machined drug delivery and sensing device into the patient, contacting said molecules in said first stage of said sensing reservoir with said molecules in said second stage of said sensing reservoir so as to form a sensing element by disintegrating said reservoir partition, said first stage and said second stage of said sensing reservoir combining to form a volume; permitting body fluid to enter said volume where said body fluid reacts with said sensing element to produce a signal detected by said sensing electrodes; sending said detected signal to control circuitry, said control circuitry sending a signal to at least one drug release reservoir in response to said detected signal received by said control circuitry; contacting said molecules in said first stage of said drug release reservoir with said molecules in said second stage of said drug release reservoir so as to form a mixture; and releasing said mixture from said micro-machined drug delivery system into said patient.

In each micro-machined device and method, the sensors may be, but are not limited to, electrochemical detection systems or optical detection systems where technological advances can use fluorescent or surface reaction sensors.

DETAILED DESCRIPTION OF THE PREFERRED EMBODIMENT(S)

A novel approach for the delivery of labile drugs is presented. Also presented is a novel biosensing device and a novel drug delivery and biosensing device.

Micro-machined drug delivery devices, micro-machined biosensing devices and micro-machined drug delivery and biosensing devices are fabricated using methods commonly applied to the manufacture of integrated circuits such as ultraviolet (UV) photolithography, reactive ion etching, electron beam evaporation, vapor deposition and spin casting. The micro-machined drug delivery device controls the delivery of drugs to the patient. The micro-machined biosensing device is capable of monitoring levels of chemicals in the patient, such as glucose levels. The micro-machined drug delivery and biosensing device is capable of not only sensing the level of a chemical in the patient but also of delivering an appropriate level of a chemical into the patient, for example the sensor may detect glucose levels and release insulin as necessary. Unless otherwise mentioned, the term micro-machined device shall refer to micro-machined drug delivery devices, micro-machined biosensing devices and micro-machined drug delivery and biosensing devices.

Each micro-machined device consists of a substrate, dual stage reservoirs, and a release system containing or enclosing the molecules to be delivered. Devices that control the release time of the molecules may include reservoir caps. Active devices may include control circuitry and a power source.

There are two types of dual stage reservoirs: drug delivery reservoirs and biosensing reservoirs. A biosensing reservoir is constructed similar to a drug delivery reservoir, except that the biosensing reservoir has a pair of sensing electrodes and is typically covered with a semi-permeable membrane that keeps the contents of the reservoir from escaping from the device but also permits fluids from the patient to enter the reservoir. Micro-machined devices that employ drug delivery reservoirs are called micro-machined drug delivery devices. Micro-machined devices employing biosensing reservoirs are called micro-machined biosensing devices. Micro-machined devices employing both types of reservoirs are called micro-machined drug delivery and biosensing devices.

METHOD OF FABRICATION: DRUG DELIVERY RESERVOIRS

Micro-machined drug delivery devices of the present invention may be constructed using a Si microfabrication approach as detailed in U.S. Pat. No. 5,368,704 to Madou et al. and is incorporated herein by reference. Referring now to FIGS. 1 through 12, the process for constructing a micro-machined drug delivery device of the present invention is illustrated.

Figure 1:
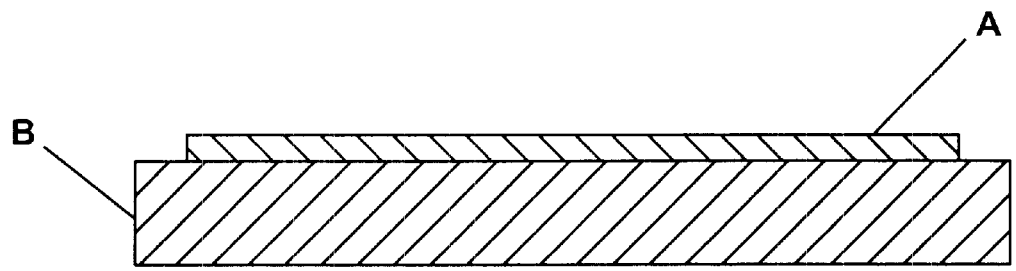
FIG. 1 shows the first step in constructing a micro-machined drug delivery device in accordance with one embodiment of the present invention.

As shown in FIG. 1, a sacrificial organic polymer film a is spin-coated on a flat solid support b. The thickness of the sacrificial layer a is between 1 and 25 micrometers. The flat solid support b is typically an optically flat plate such as a silicon wafer, a glass plate or a quartz plate. The sacrificial layer a is typically made of a water-soluble polymer, although organic solvent soluble polymers are usable too. Suitable water soluble polymers include, but are not limited to: natural polymers such as: starches, gums, albumin, gluten, gelatin, and other proteins; semisynthetic polymers such as: cellulose ethers and starch derivatives; and synthetic polymers such as polyacrylamide, poly(oxyethylene), PVA, PVP, poly(acrylic acid), poly(phosphoric acid), poly (styrene sulphonic acid), poly(4-vinyl pyridine), and poly (vinylamine).

Figure 2:
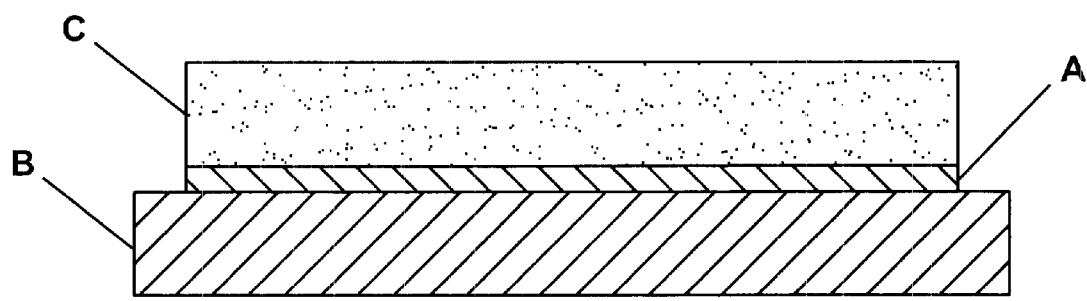
FIG. 2 shows a subsequent step in the formation of a micro-machined drug delivery device in accordance with one embodiment of the present invention.
Figure 3:
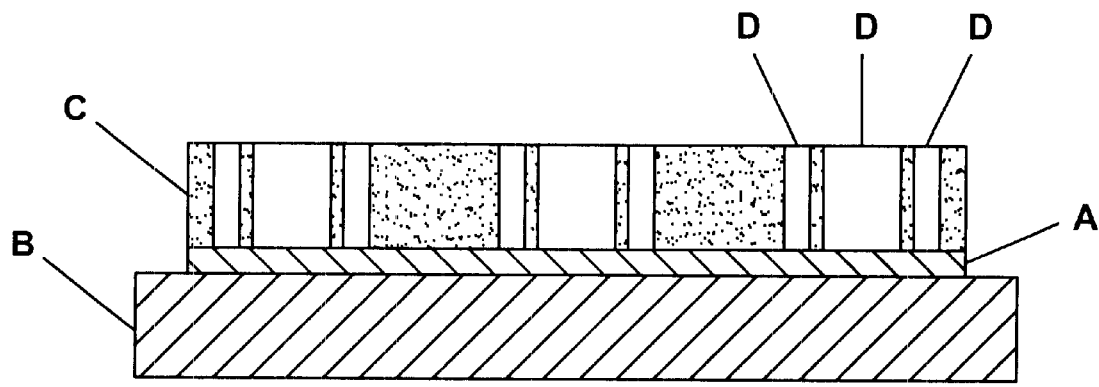
FIG. 3 shows a subsequent step in the formation of a micro-machined drug delivery device in accordance with one embodiment of the present invention.

As in FIG. 2, a layer of deep UV negative photoresist c is applied over the sacrificial thin film a by spin coating. The thickness of the negative photoresist c is typically between 1 and 10 micrometers. Suitable UV negative photoresists include: SU-8 and polyimides. The UV negative photoresist c is then exposed and developed to produce electrolyte contact holes (shown in FIG. 3 as element d).

Figure 4:
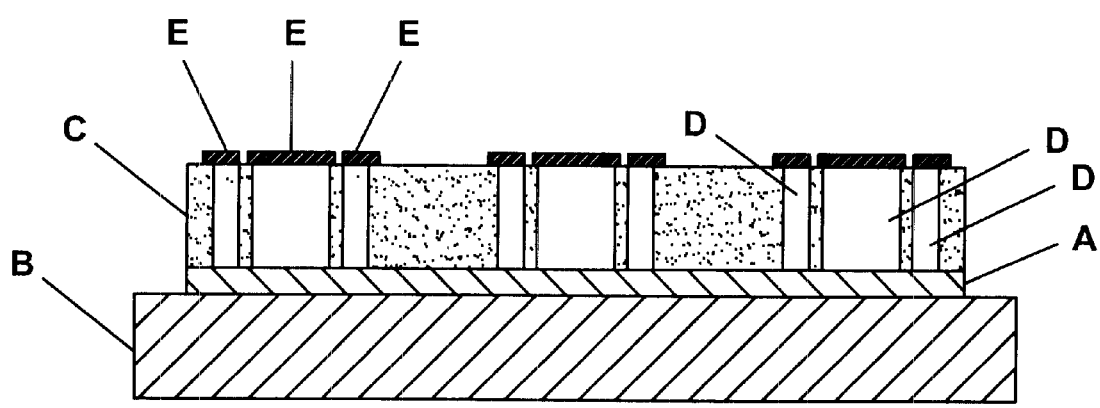
FIG. 4 shows a subsequent step in the formation of a micro-machined drug delivery device in accordance with one embodiment of the present invention.

After creation of the electrolyte contact holes d, electrodes e are deposited as shown in FIG. 4. The electrodes e act as reservoir caps for the release of the molecules from the micro-machined device. All of the electrodes e are preferably constructed of the same metal. One choice is silver. Other suitable metals include iron and titanium. A thin layer of titanium, chromium or other adhesion promoting material is deposited through a shadow mask for better adhesion of subsequent metals over both the photoresist and the planarizing/sacrificial material surfaces (not shown). This thin layer of metal can be deposited by sputtering or evaporation, although sputtering is preferred.

Figure 5:
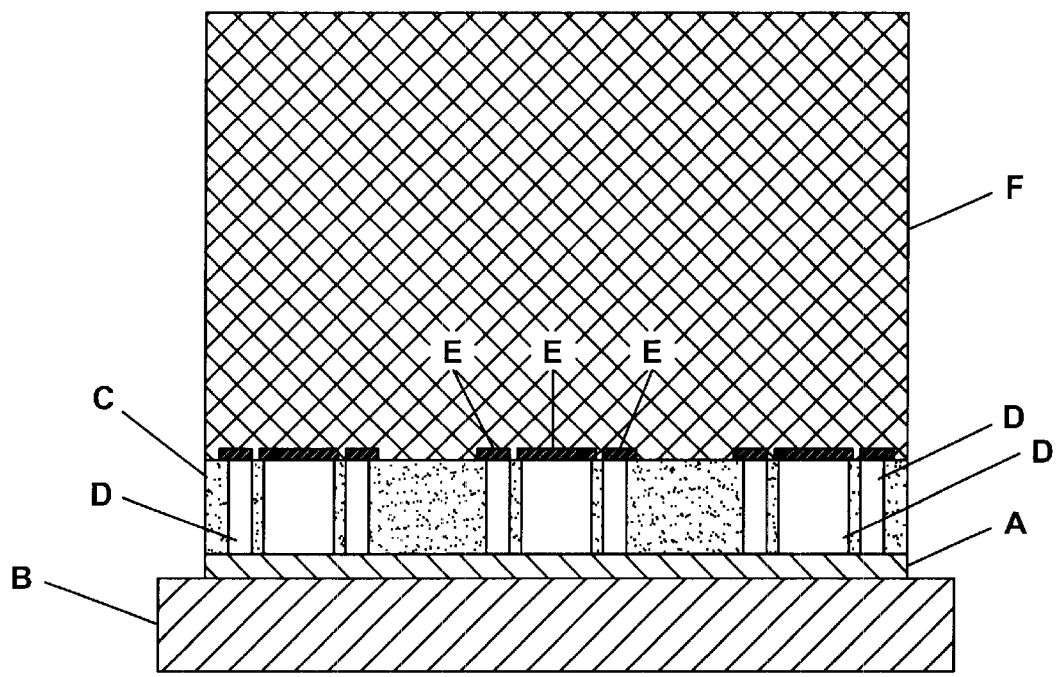
FIG. 5 shows a subsequent step in the formation of a micro-machined drug delivery device in accordance with one embodiment of the present invention.
Figure 6:
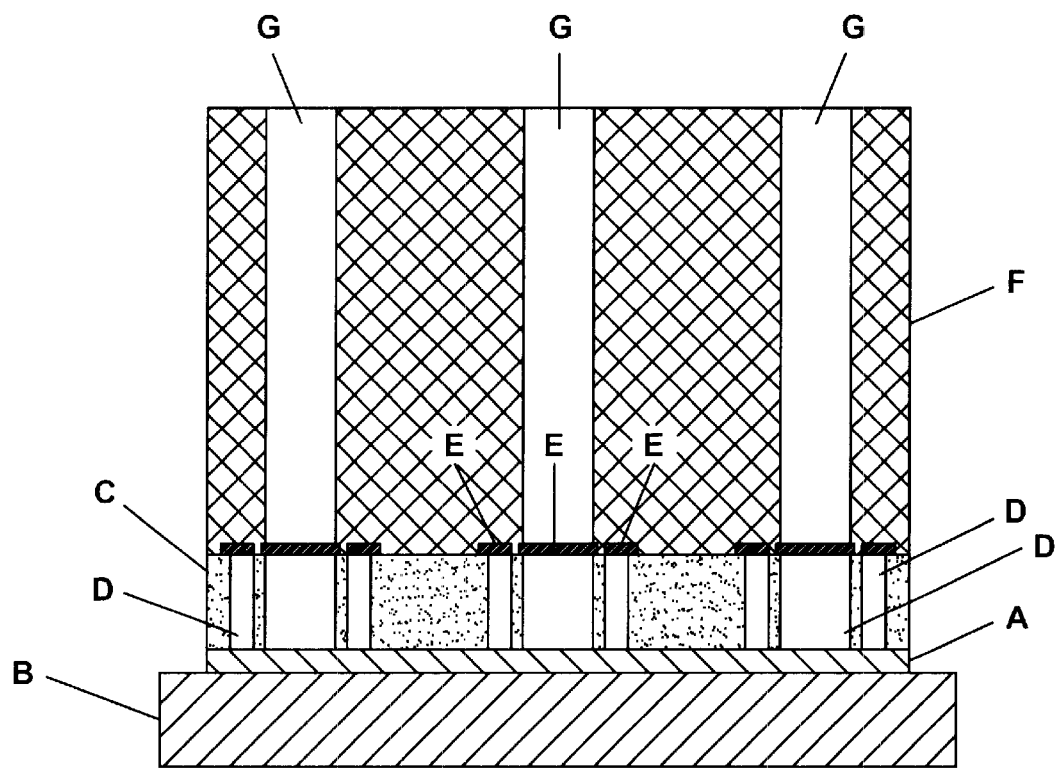
FIG. 6 shows a subsequent step in the formation of a micro-machined drug delivery device in accordance with one embodiment of the present invention.

A thick layer of UV photoresist f is spin-coated or cast over the metal electrode patterns e as shown in FIG. 5. The thickness of this layer of UV photoresist can range from 100 to 500 micrometers. The UV photoresist f is typically made from the same materials as above, which includes SU-8 and polyimides. The UV photoresist f is exposed and developed to create drug reservoirs g, as illustrated in FIG. 6. These reservoirs are referred to as second stage reservoirs.

A two-step process may be used to develop the reservoirs. The two-step process permits the shape of the reservoirs to be varied. For example, a reservoir may be constructed with a narrow opening (a neck) against the metal electrode and a wider profile for the rest of the reservoir.

Figure 7:
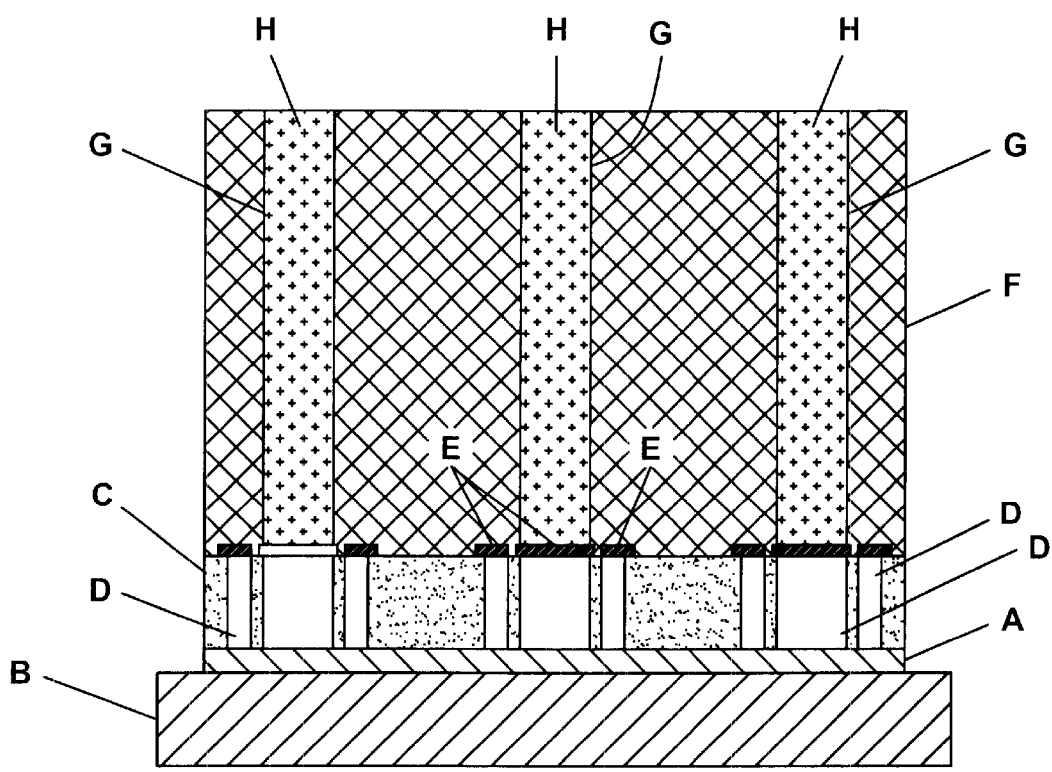
FIG. 7 shows a subsequent step in the formation of a micro-machined drug delivery device in accordance with one embodiment of the present invention.

As shown in FIG. 7, the reservoirs g are filled with drugs h. For liquid drugs, the filling process is accomplished using an automated drop delivery system. Solid drugs may be placed into the reservoirs by any suitable method.

Figure 8:
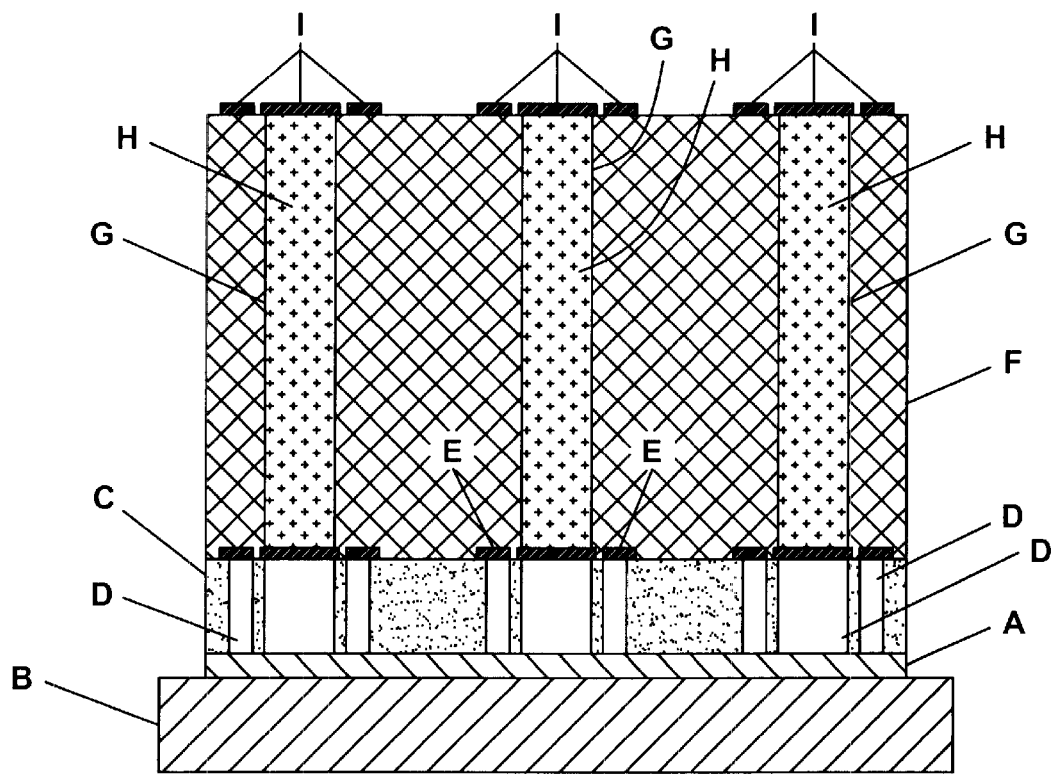
FIG. 8 shows a subsequent step in the formation of a micro-machined drug delivery device in accordance with one embodiment of the present invention.

FIG. 8 shows reservoir partitions i deposited after filling the reservoirs g with drugs h. The reservoir partition is preferably made of the same material as the reservoir cap. One preferred material is silver, although other suitable materials include iron and titanium.

Figure 9:
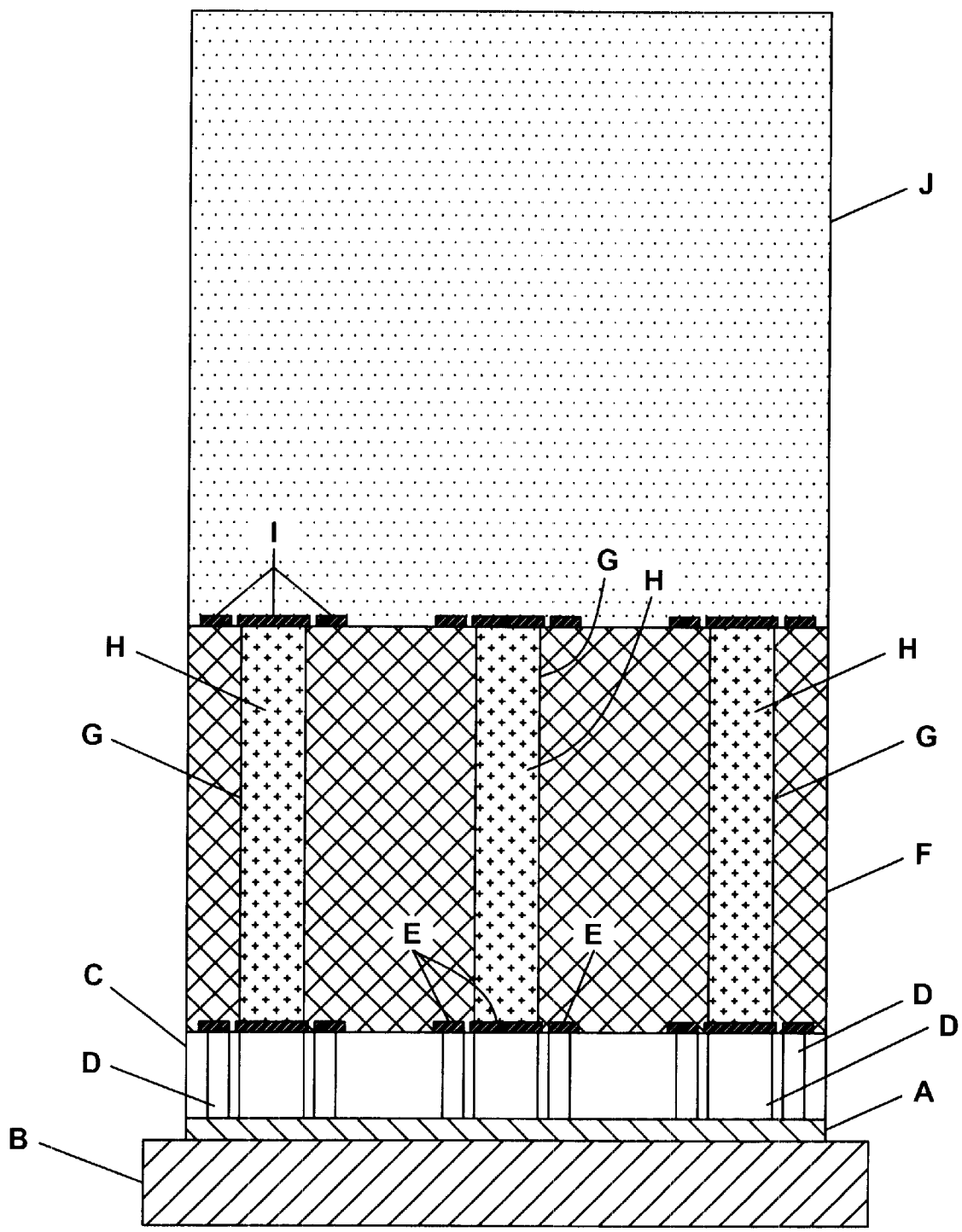
FIG. 9 shows a subsequent step in the formation of a micro-machined drug delivery device in accordance with one embodiment of the present invention.
Figure 10:
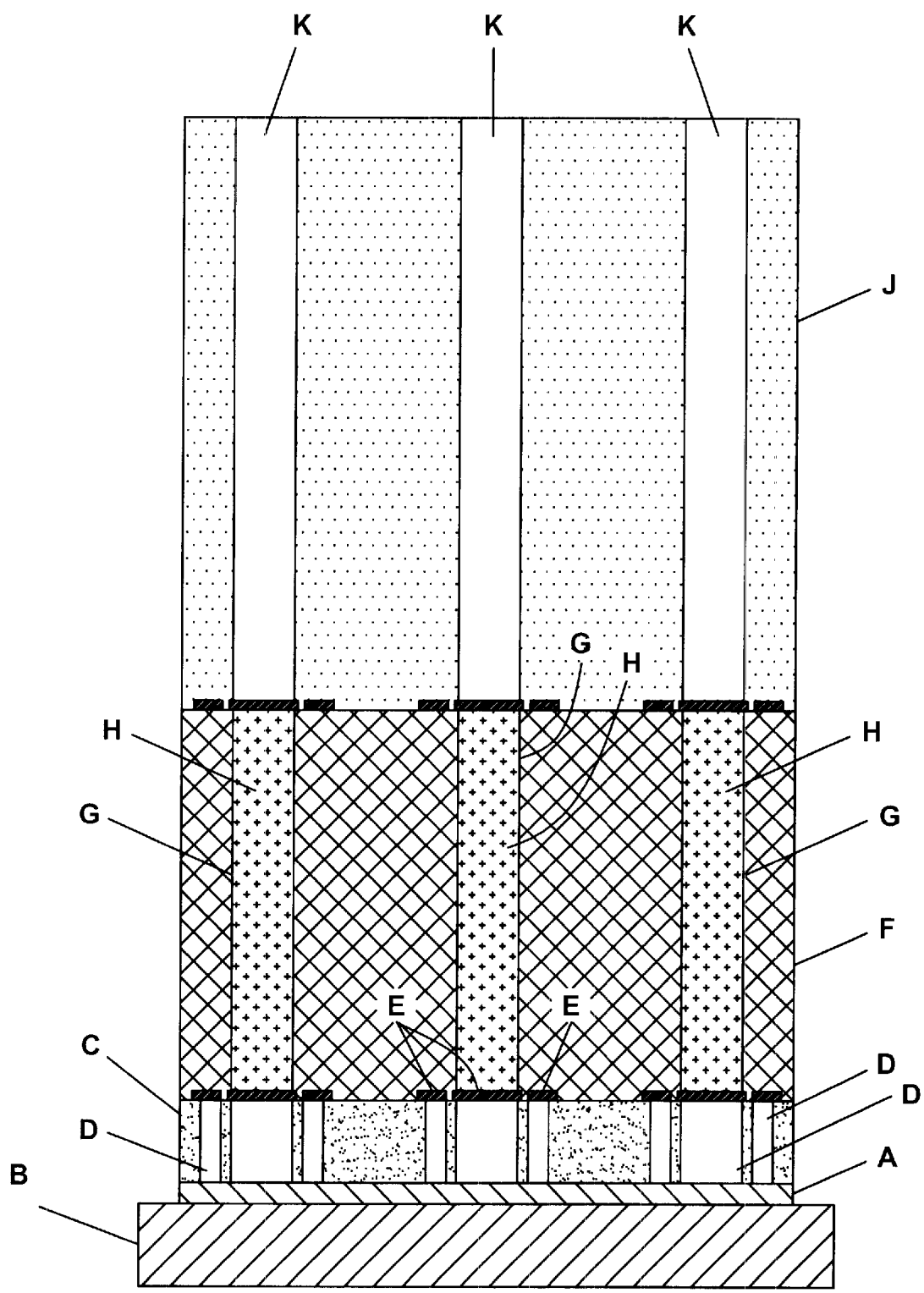
FIG. 10 shows a subsequent step in the formation of a micro-machined drug delivery device in accordance with one embodiment of the present invention.

FIG. 9 shows a second thick layer of photoresist j spin coated or cast over the reservoir partitions i. The thickness of the second thick layer of photoresist j can range from 100 to 500 micrometers. The UV photoresist j is typically made form the same materials as above, which includes SU-8 and polyimides. The UV photoresist j is exposed and developed to create drug reservoirs k, as shown in FIG. 10. These reservoirs k are referred to as the first stage.

Figure 11:
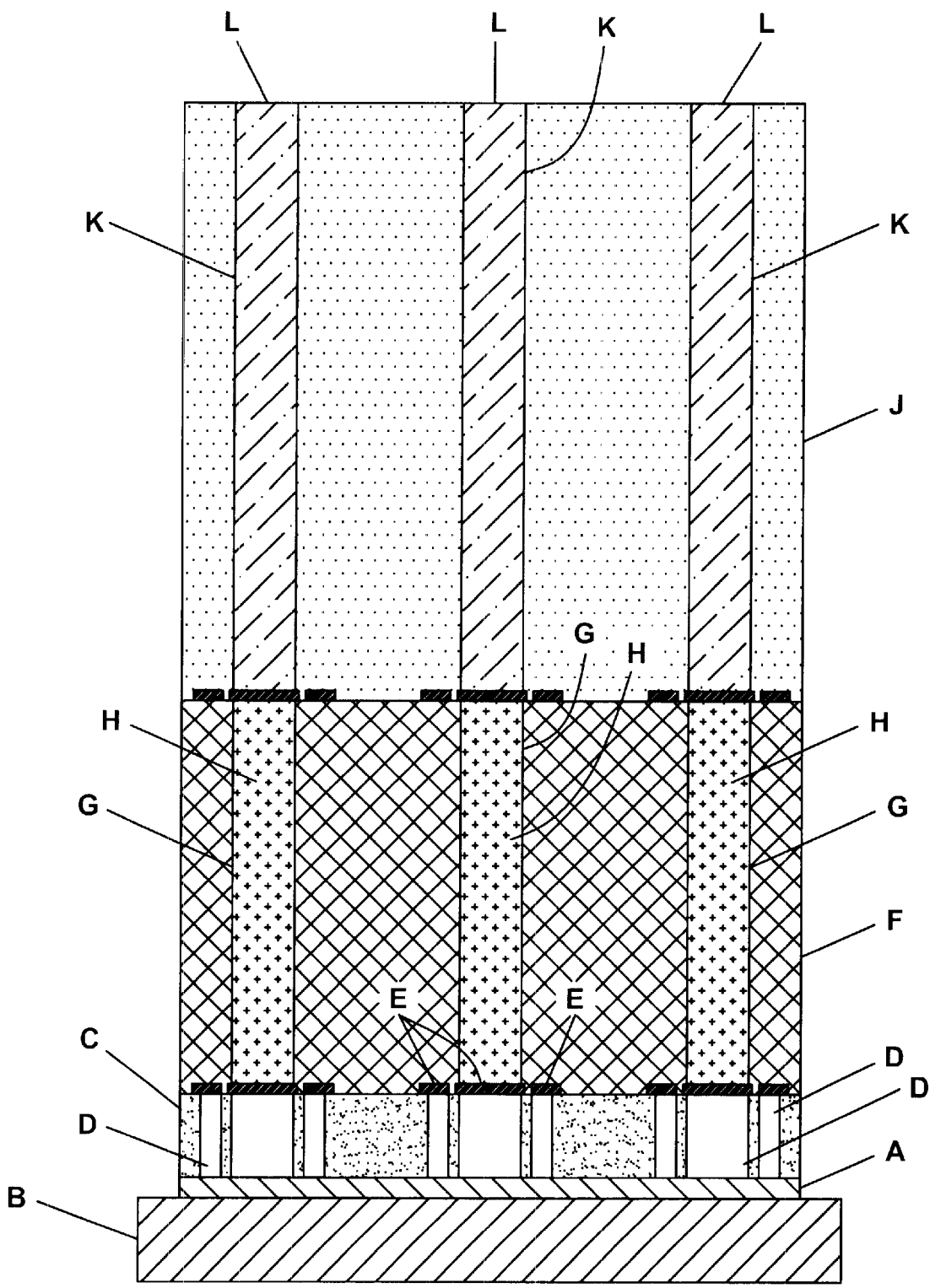
FIG. 11 shows a subsequent step in the formation of a micro-machined drug delivery device in accordance with one embodiment of the present invention.
Figure 12:
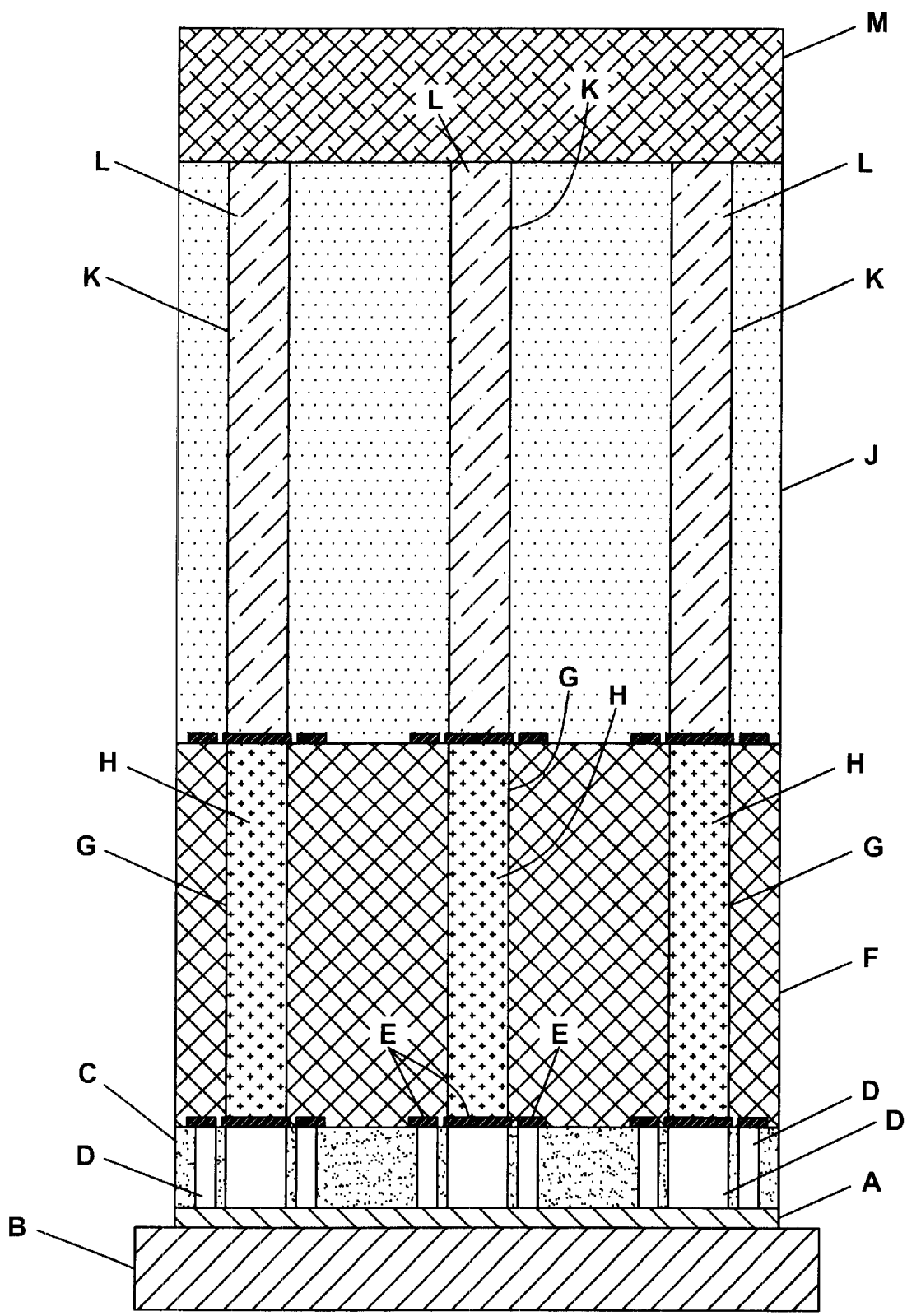
FIG. 12 shows a subsequent step in the formation of a micro-machined drug delivery device in accordance with one embodiment of the present invention.

As shown in FIG. 11 the reservoirs k are filled with drugs l. After filling the reservoirs k with drugs l, the reservoirs are sealed as shown in FIG. 12. Preferably, the reservoirs k are sealed using a low temperature lamination technique. A good seal ensures a longer shelf life. A preferred lamination technique involves using a dry sheet photoresist m such as Riston that is exposed to UV light for curing and sealing in-situ.

To complete the fabrication of the micro-machined device, the device is released from the support by dissolving the sacrificial layer on the support plate and the sacrificial material above the metal electrodes (reservoir caps). Preferably, both layers are dissolved in a single step.

METHOD OF FABRICATION: SENSING RESERVOIRS

Micro-machined sensing devices of the present invention may be constructed using a Si microfabrication approach as detailed in U.S. Pat. No. 5,368,704 to Madou et al. and is incorporated herein by reference. Referring now to FIGS. 13 through 24, the process for constructing a micro-machined sensing device of the present invention is illustrated.

Figure 13:
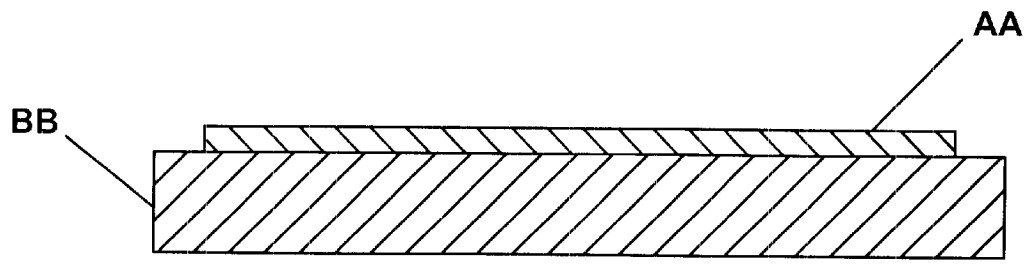
FIG. 13 shows the first step in constructing a micro-machined sensing device in accordance with one embodiment of the present invention.

As shown in FIG. 13, a sacrificial organic polymer film aa is spin-coated on a flat solid support bb. The thickness of the sacrificial layer aa is between 1 and 25 micrometers. The flat solid support bb is typically an optically flat plate such as a silicon wafer, a glass plate or a quartz plate. The sacrificial layer aa is typically made of a water-soluble polymer, although organic solvent soluble polymers are usable too. Suitable water soluble polymers include, but are not limited to: natural polymers such as: starches, gums, albumin, gluten, gelatin, and other proteins; semisynthetic polymers such as: cellulose ethers and starch derivatives; and synthetic polymers such as polyacrylamide, poly(oxyethylene), PVA, PVP, poly(acrylic acid), poly(phosphoric acid), poly (styrene sulphonic acid), poly(4-vinyl pyridine), and poly (vinylamine).

Figure 14:
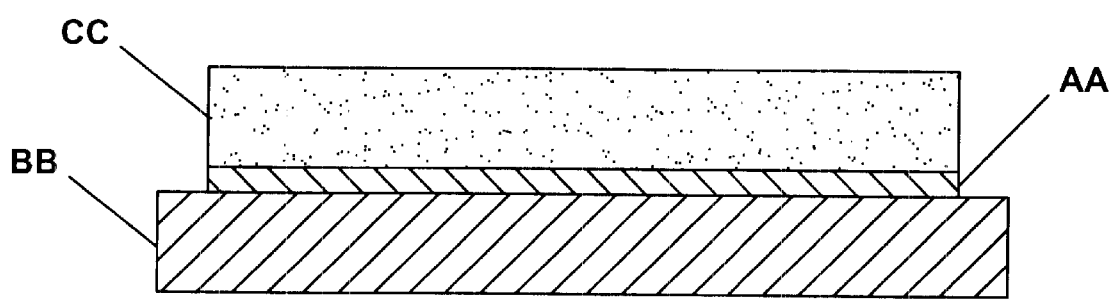
FIG. 14 shows a subsequent step in the formation of a micro-machined sensing device in accordance with one embodiment of the present invention.
Figure 15:
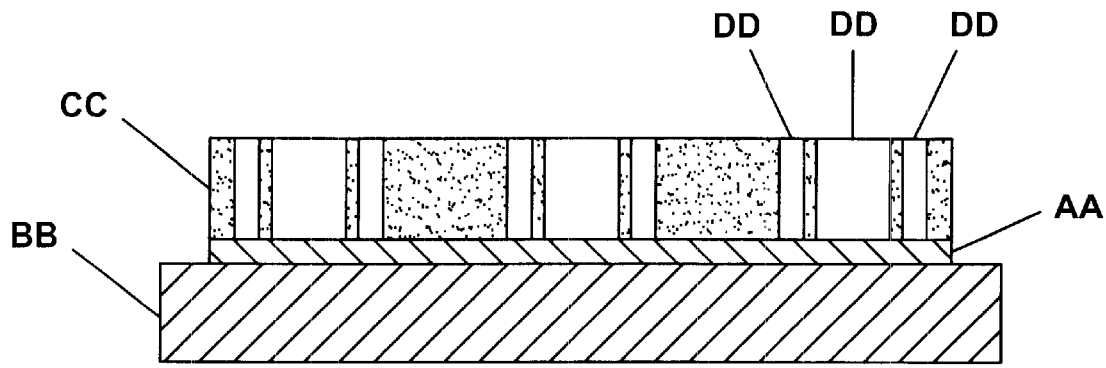
FIG. 15 shows a subsequent step in the formation of a micro-machined sensing device in accordance with one embodiment of the present invention.

As in FIG. 14, a layer of deep UV negative photoresist cc is applied over the sacrificial thin film aa by spin coating. The thickness of the negative photoresist cc is typically between 1 and 10 micrometers. Suitable UV negative photoresists include: SU-8 and polyimides. The UV negative photoresist cc is then exposed and developed to produce electrolyte contact holes (shown in FIG. 15 as element dd).

Figure 16:
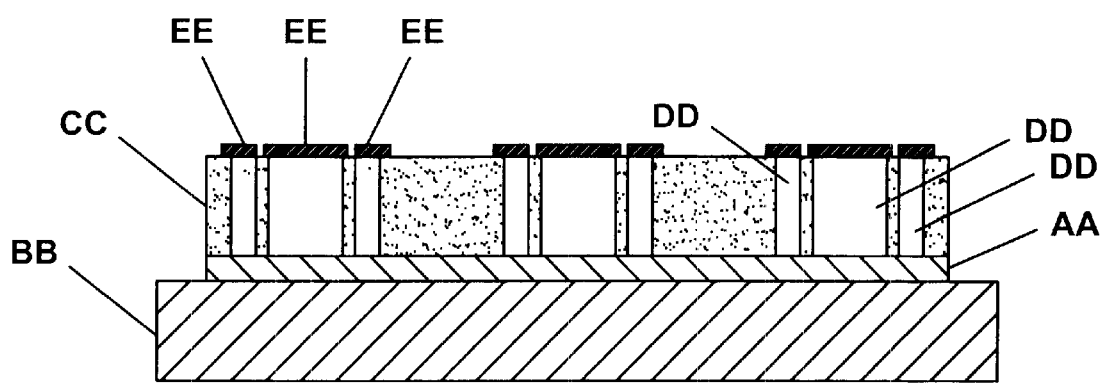
FIG. 16 shows a subsequent step in the formation of a micro-machined sensing device in accordance with one embodiment of the present invention.

After creation of the electrolyte contact holes dd, electrodes ee are deposited as shown in FIG. 16. The electrodes ee act as reservoir caps for the release of the molecules from the micro-machined device. All of the electrodes ee are preferably constructed of the same metal. One choice is silver. Other suitable metals include iron and titanium. A thin layer of titanium, chromium or other adhesion promoting material is deposited through a shadow mask for better adhesion of subsequent metals over both the photoresist and the planarizing/sacrificial material surfaces (not shown). This thin layer of metal can be deposited by sputtering or evaporation, although sputtering is preferred.

Figure 17:
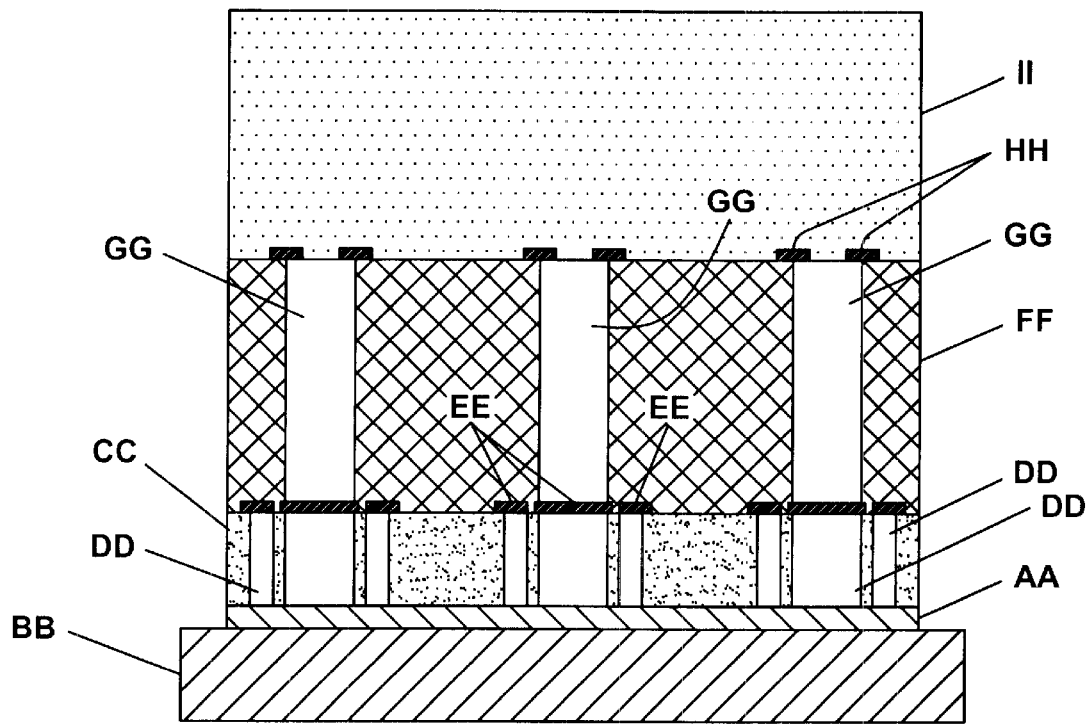
FIG. 17 shows a subsequent step in the formation of a micro-machined sensing device in accordance with one embodiment of the present invention.
Figure 18:
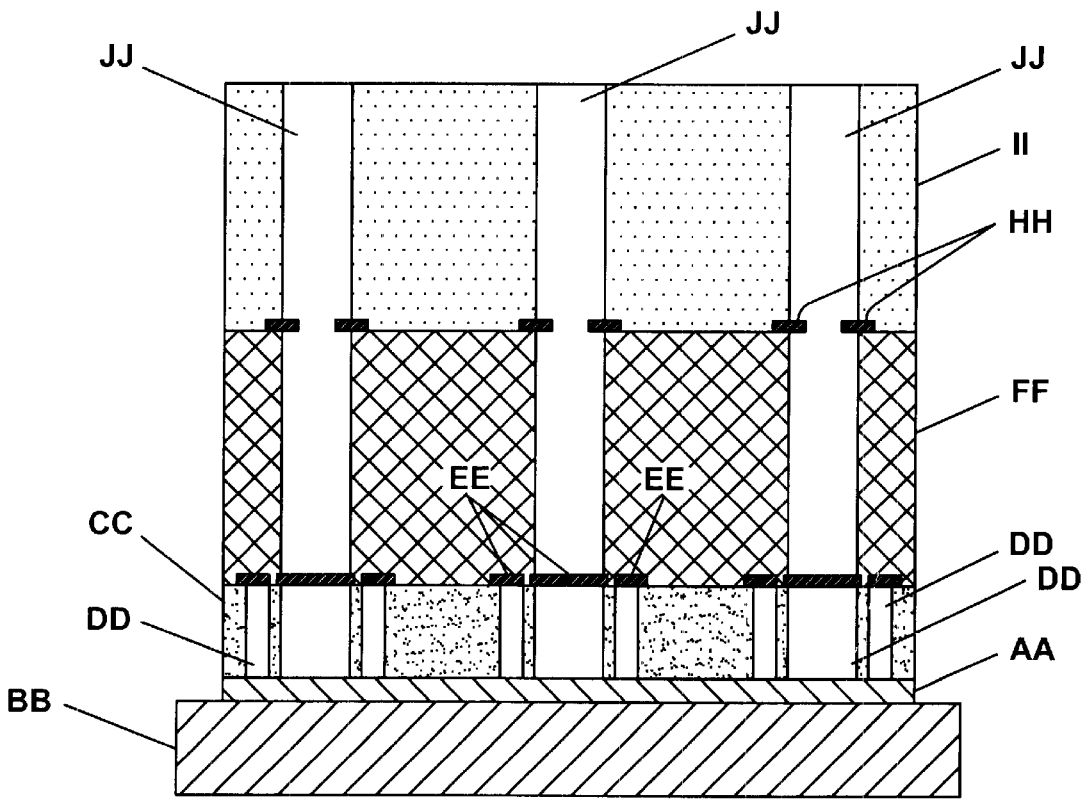
FIG. 18 shows a subsequent step in the formation of a micro-machined sensing device in accordance with one embodiment of the present invention.

With respect to FIG. 17, a thick layer of UV photoresist ff is spin-coated or cast over the metal electrode patterns ee, exposed and developed to create partial reservoirs gg. After creating the partial reservoirs gg, sensing electrodes hh are deposited before another layer of UV photoresist ii is added. The UV photoresist ii is exposed and developed to create drug reservoirs jj, as illustrated in FIG. 18. These reservoirs gg are referred to as second stage reservoirs.

A two-step process may be used to develop the reservoirs. The two-step process permits the shape of the reservoirs to be varied. For example, a reservoir may be constructed with a narrow opening (a neck) against the metal electrode and a wider profile for the rest of the reservoir.

Figure 19:
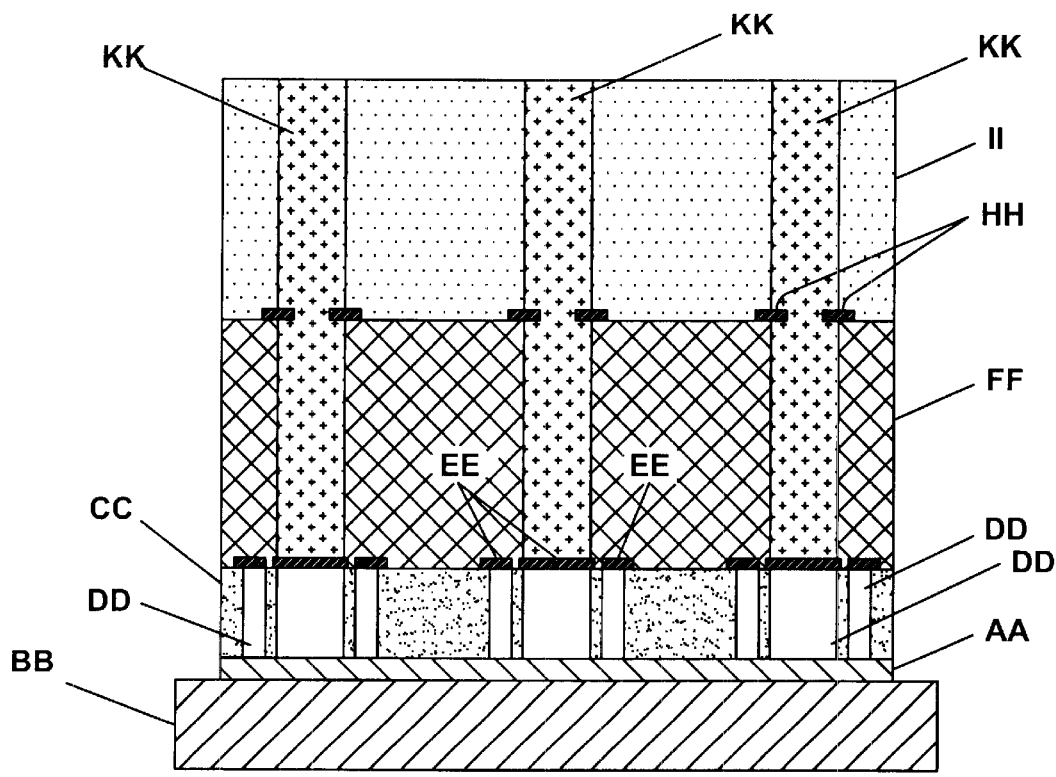
FIG. 19 shows a subsequent step in the formation of a micro-machined sensing device in accordance with one embodiment of the present invention.

As shown in FIG. 19, the reservoirs jj are filled with drugs kk. For liquid drugs, the filling process is accomplished using an automated drop delivery system. Solid drugs may be placed into the reservoirs by any suitable method.

Figure 20:
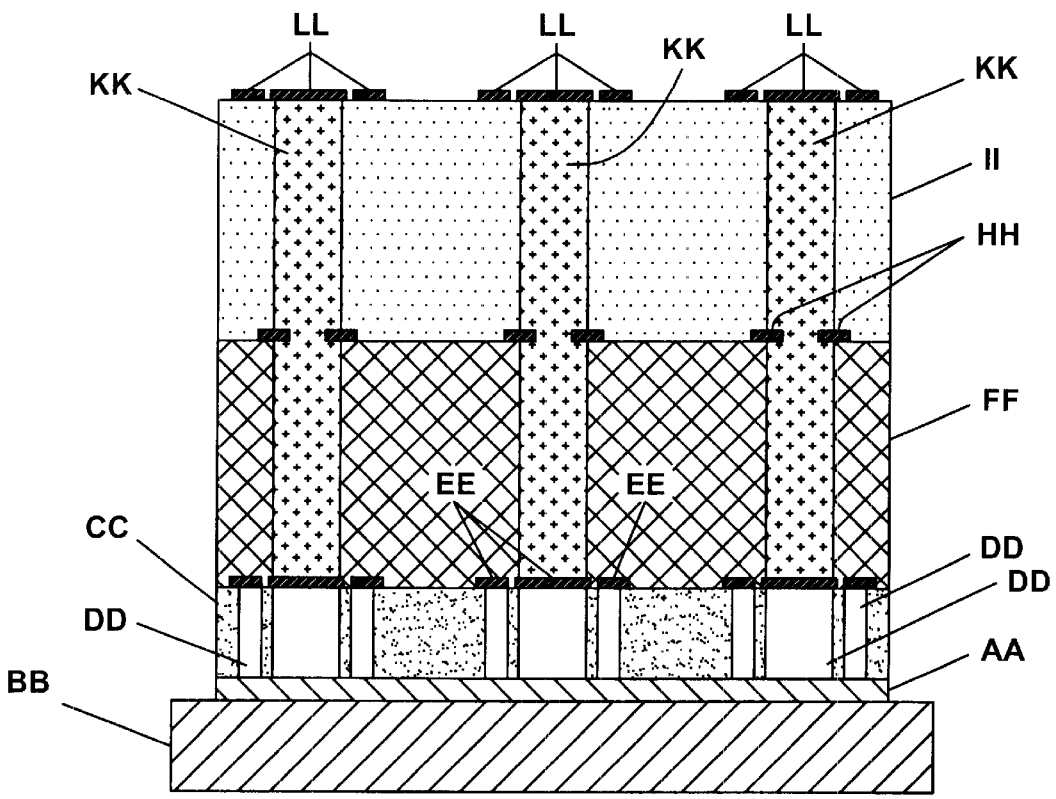
FIG. 20 shows a subsequent step in the formation of a micro-machined sensing device in accordance with one embodiment of the present invention.

FIG. 20 shows reservoir partitions ll deposited after filling the reservoirs jj with drugs kk. The reservoir partitions ll are preferably made of the same material as the reservoir caps ee. One preferred material is silver, although other suitable materials include iron and titanium.

Figure 21:
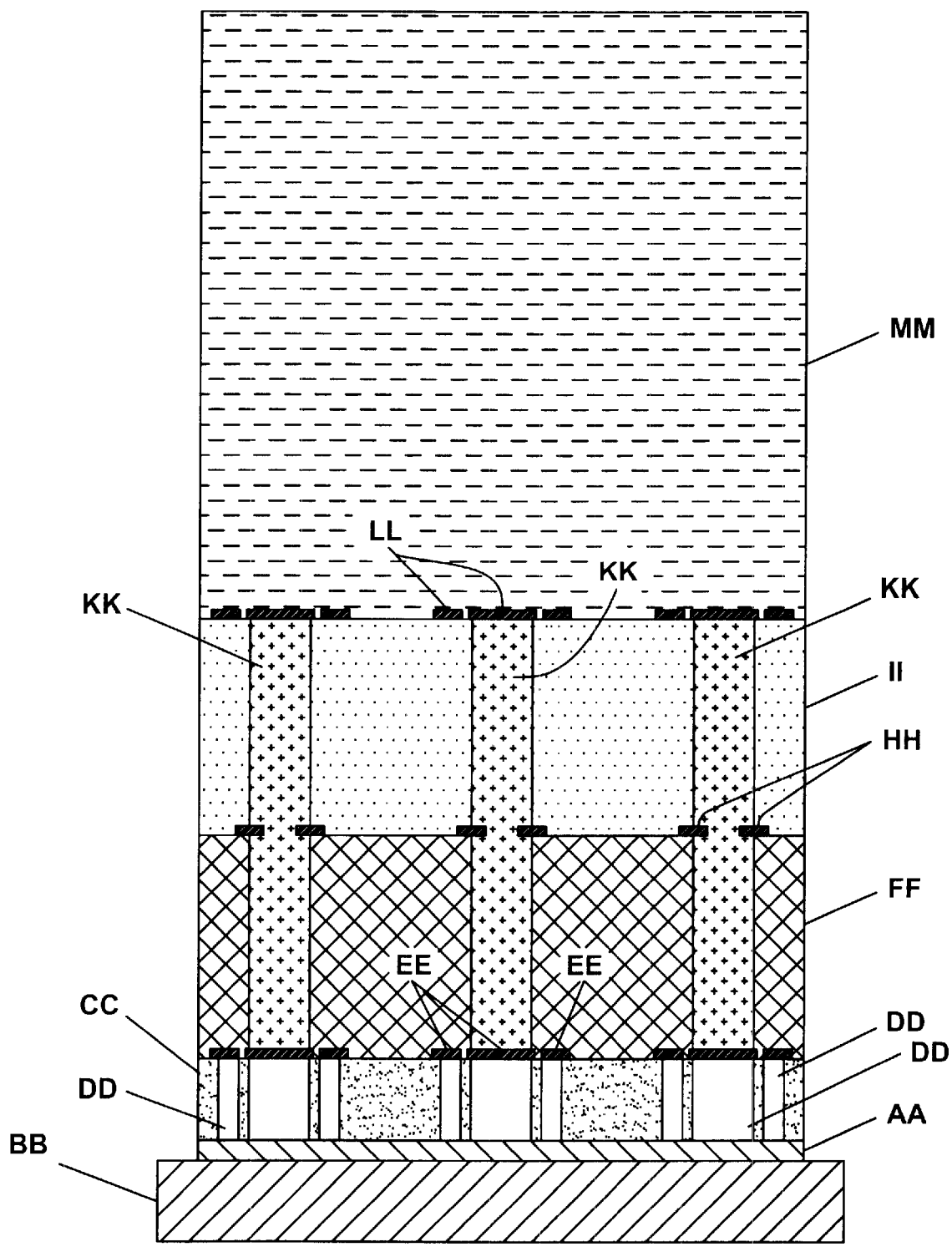
FIG. 21 shows a subsequent step in the formation of a micro-machined sensing device in accordance with one embodiment of the present invention.
Figure 22:
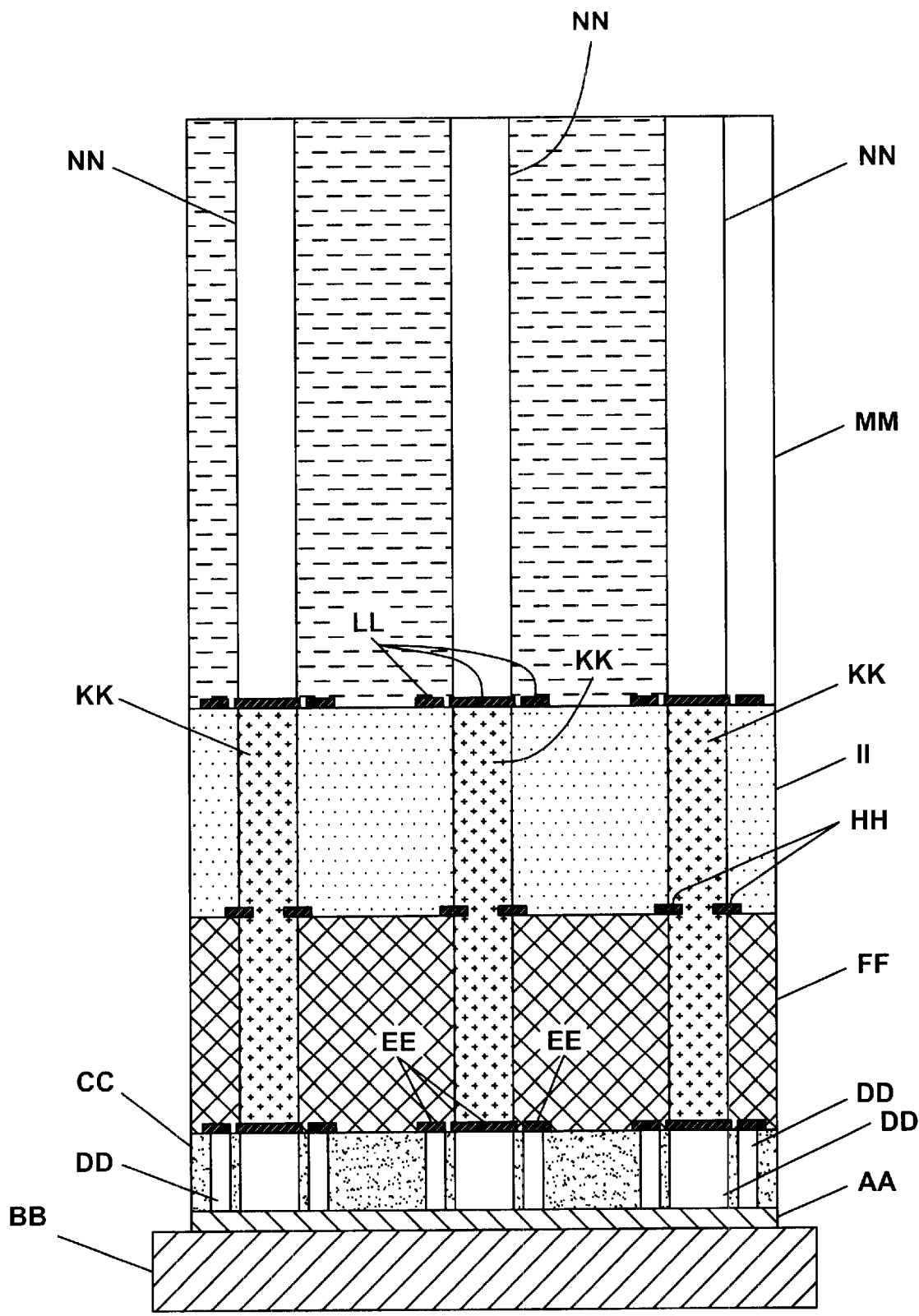
FIG. 22 shows a subsequent step in the formation of a micro-machined sensing device in accordance with one embodiment of the present invention.

FIG. 21 shows a second thick layer of photoresist mm spin coated or cast over the reservoir partitions ll. The thickness of the second thick layer of photoresist mm can range from 100 to 500 micrometers. The UV photoresist mm is typically made from the same materials as above, which includes SU-8 and polyimides. The UV photoresist mm is exposed and developed to create drug reservoirs nn, as shown in FIG. 22. These reservoirs nn are referred to as first stage.

Figure 23:
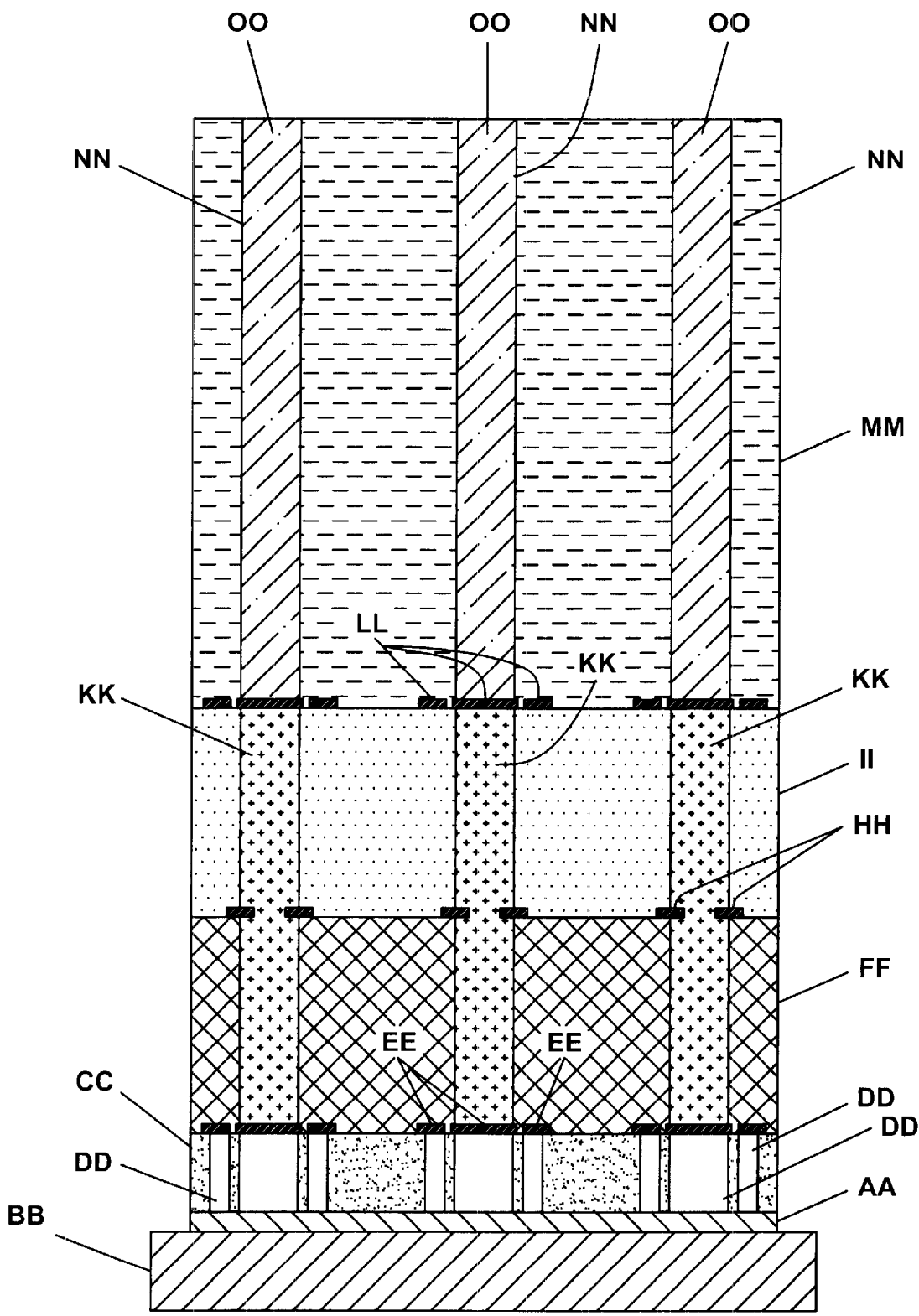
FIG. 23 shows a subsequent step in the formation of a micro-machined sensing device in accordance with one embodiment of the present invention.
Figure 24:
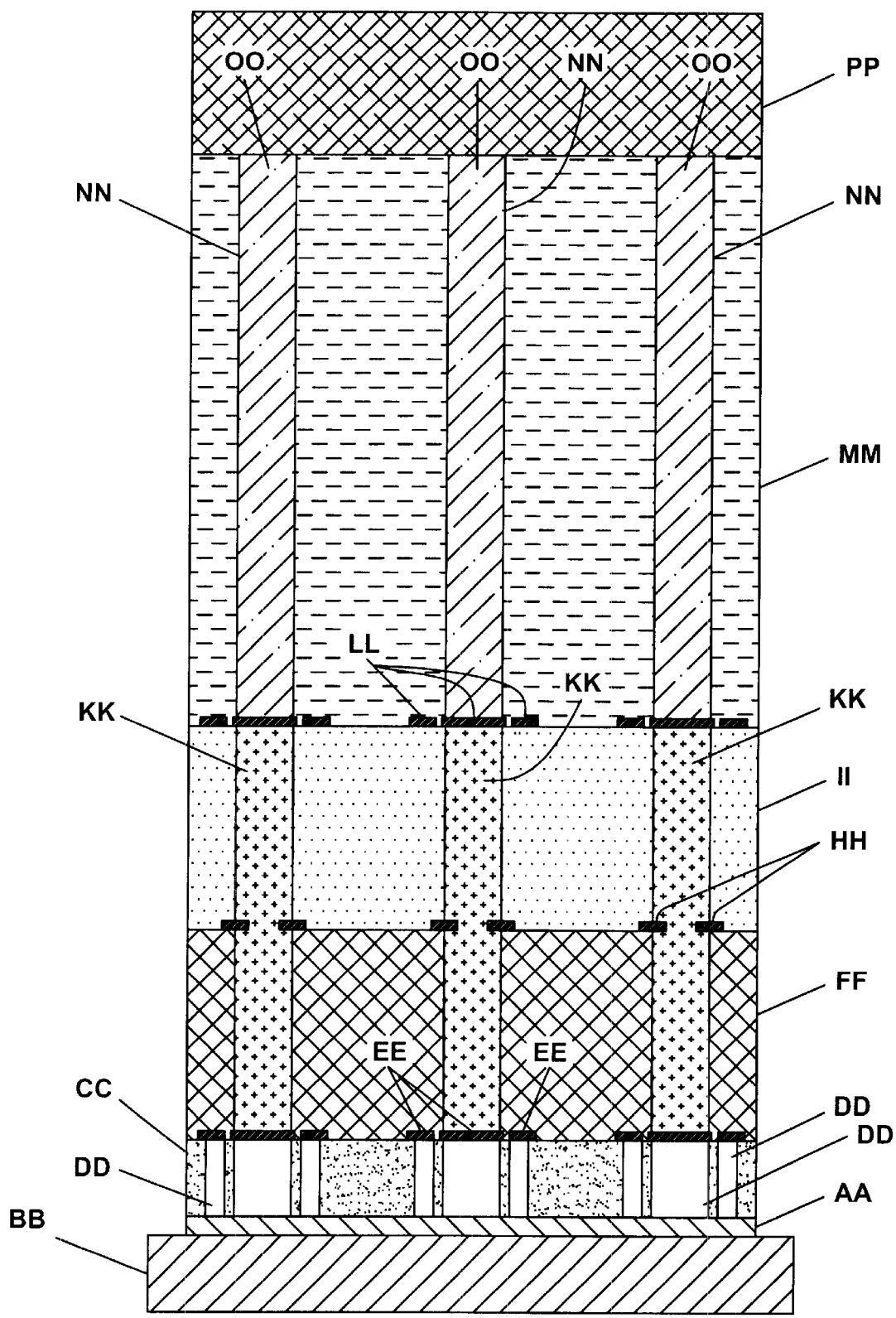
FIG. 24 shows a subsequent step in the formation of a micro-machined sensing device in accordance with one embodiment of the present invention.

As shown in FIG. 23 the reservoirs nn are filled with drugs oo. After filling the reservoirs nn with drugs oo, the reservoirs nn are sealed as shown in FIG. 24. Preferably, the reservoirs nn are sealed using a low temperature lamination technique. A good seal ensures a longer shelf life. A preferred lamination technique involves using a dry sheet photoresist pp such as Riston that is exposed to UV light for curing and sealing in-situ.

To complete the fabrication of the micro-machined device, the device is released from the support by dissolving the sacrificial layer on the support plate and the sacrificial material above the metal electrodes (reservoir caps). Preferably, both layers are dissolved in a single step.

METHOD OF FABRICATION: CONNECTING RESERVOIRS

To connect the arrays of reservoirs to the control circuitry of the device, one of two known methods are preferred. The first method based on flex circuit technology is advantageous for less dense arrays. The second method based on dry resist lithography is advantageous for higher density arrays. The individual reservoirs, whether sensor-type or drug delivery-type are electronically connected to a control unit.

A control unit typically comprises circuitry, a microprocessor and a battery.

EXAMPLE 1

Sensor

Figure 25:
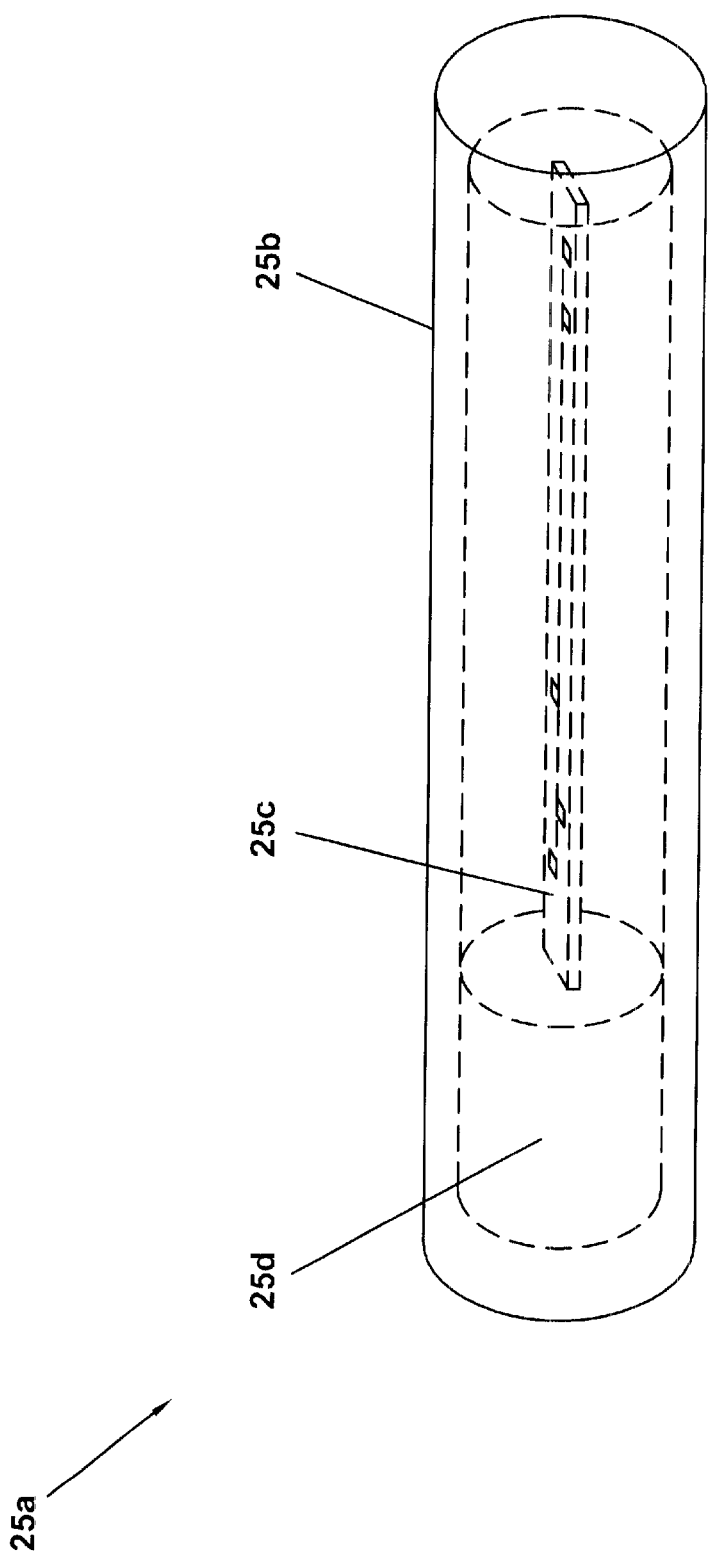
FIG. 25 shows a micro-machined sensing device in accordance with one embodiment of the present invention.

With respect to FIG. 25, a micro-machined sensing device of the present invention is depicted. The micro-machined sensing device 25a comprises a battery 25d, control circuitry 25c and an array of sensing reservoirs 25b. In this embodiment the sensing reservoirs are positioned about the periphery of the device 25a.

Figure 26:
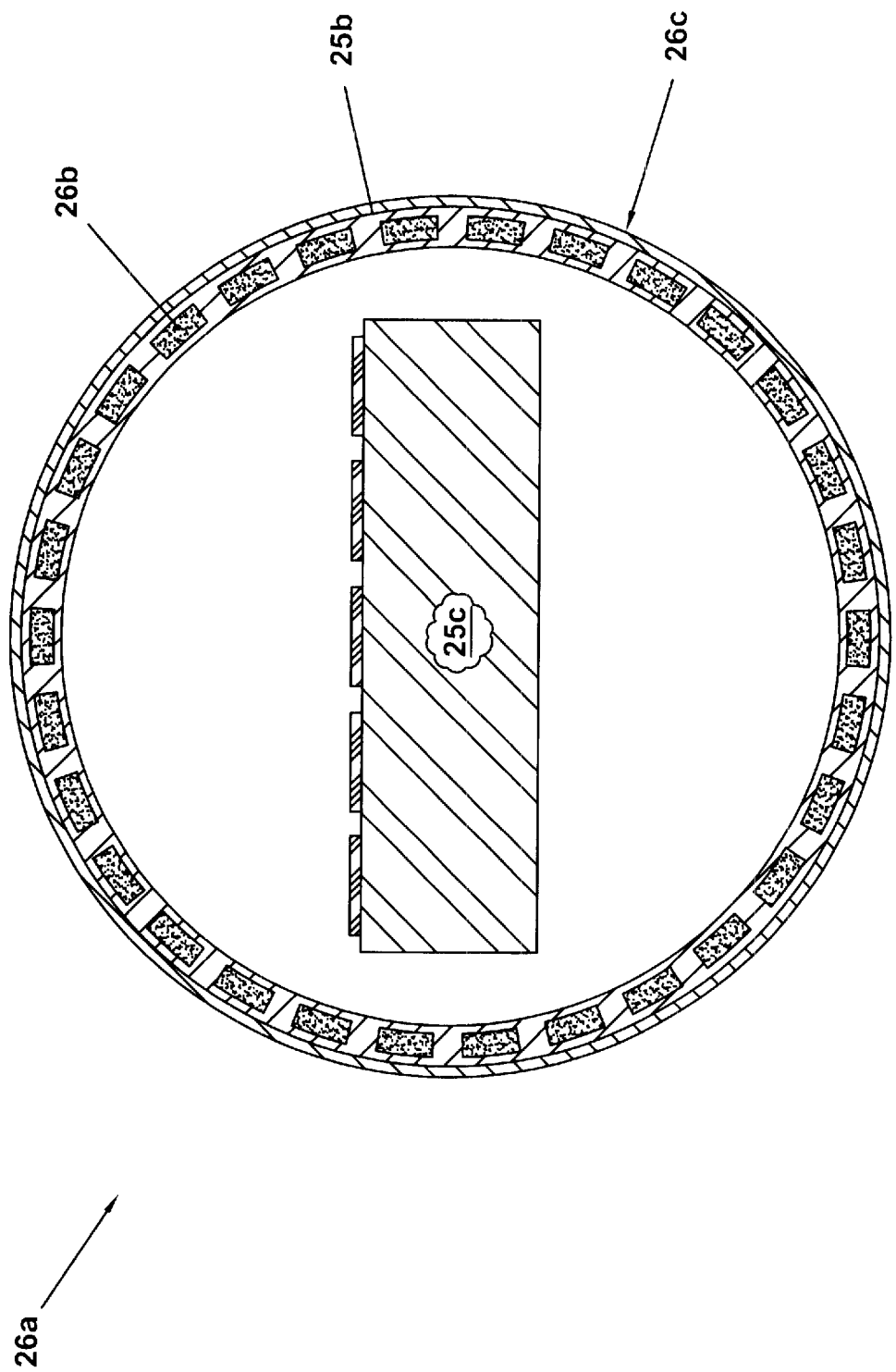
FIG. 26 shows a cross section of the device depicted in FIG. 25.

FIG. 26 shows a cross section of the micro-machined sensing device depicted in FIG. 25. The cross section 26a depicts the positioning of the sensing reservoir array 25b about the periphery of the device. The individual sensing reservoirs 26b are encapsulated by a semi-permeable membrane 26c.

Figure 27:
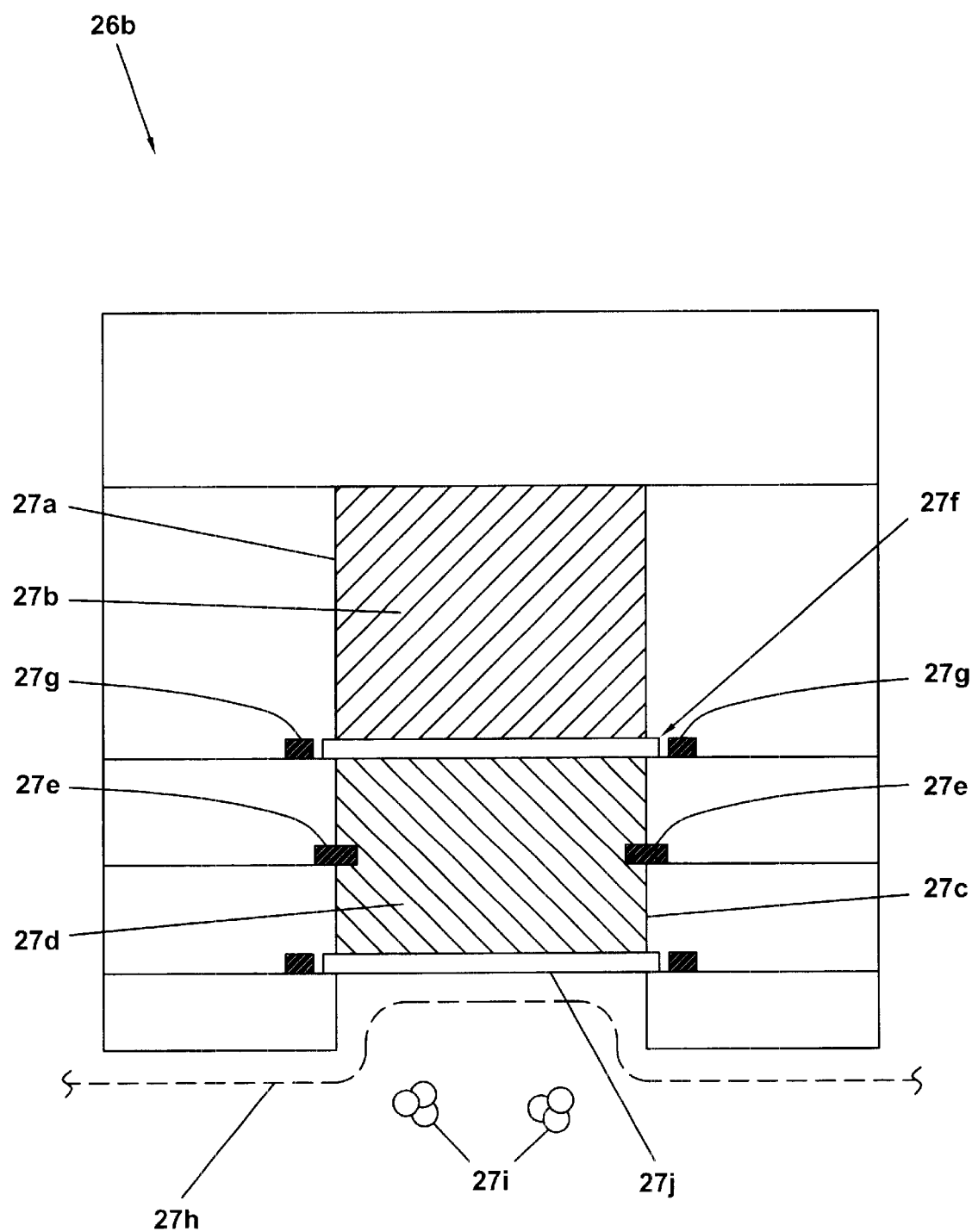
FIG. 27 shows the initial state of a sensing reservoir in accordance with one embodiment of the present invention.

FIG. 27 shows the initial state a dual stage-sensing reservoir 26b in a sensing device of the present invention. The dual stage-sensing reservoir has a first stage 27a which holds drugs 27b such as lyophilized reagents. The device has a second stage 27c which contains a buffer 27d. The preferred embodiment uses labile reagents in these sensing reservoirs. The second stage 27c also contains a sensor which may comprise a pair of sensing electrodes 27e. The first stage 27a and the second stage 27c are separated by a reservoir partition 27f. The reservoir partition 27f is in electrical communication with electrical contacts 27g. Applying a voltage via the electrical contacts 27g disintegrates the reservoir partition 27f. The disintegration of the reservoir partition 27f shall be referred to as opening. Between the reservoir cap 27j and the interstitial fluids 27i of the patient's body is a semipermeable membrane 27h.

Figure 28:
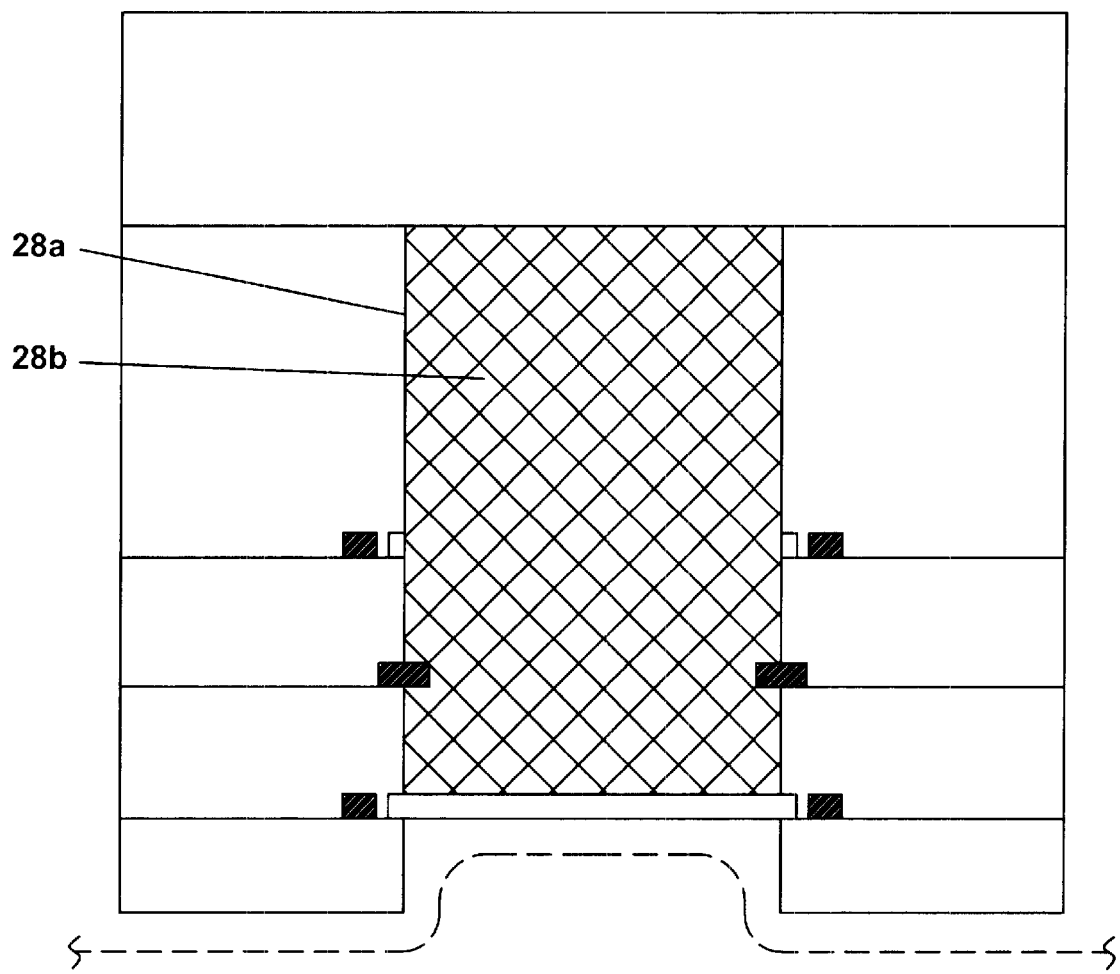
FIG. 28 shows the operation of a sensing reservoir in accordance with one embodiment of the present invention.

FIG. 28 shows the dual stage-sensing reservoir after opening the reservoir partition. The first stage 27a and the second stage 27c combine to form a volume 28a. The volume 28a is now filled with a mixture 28b of the drug 27b and the buffer 27d. The mixture 28b is a reconstituted sensing element.

Figure 29:
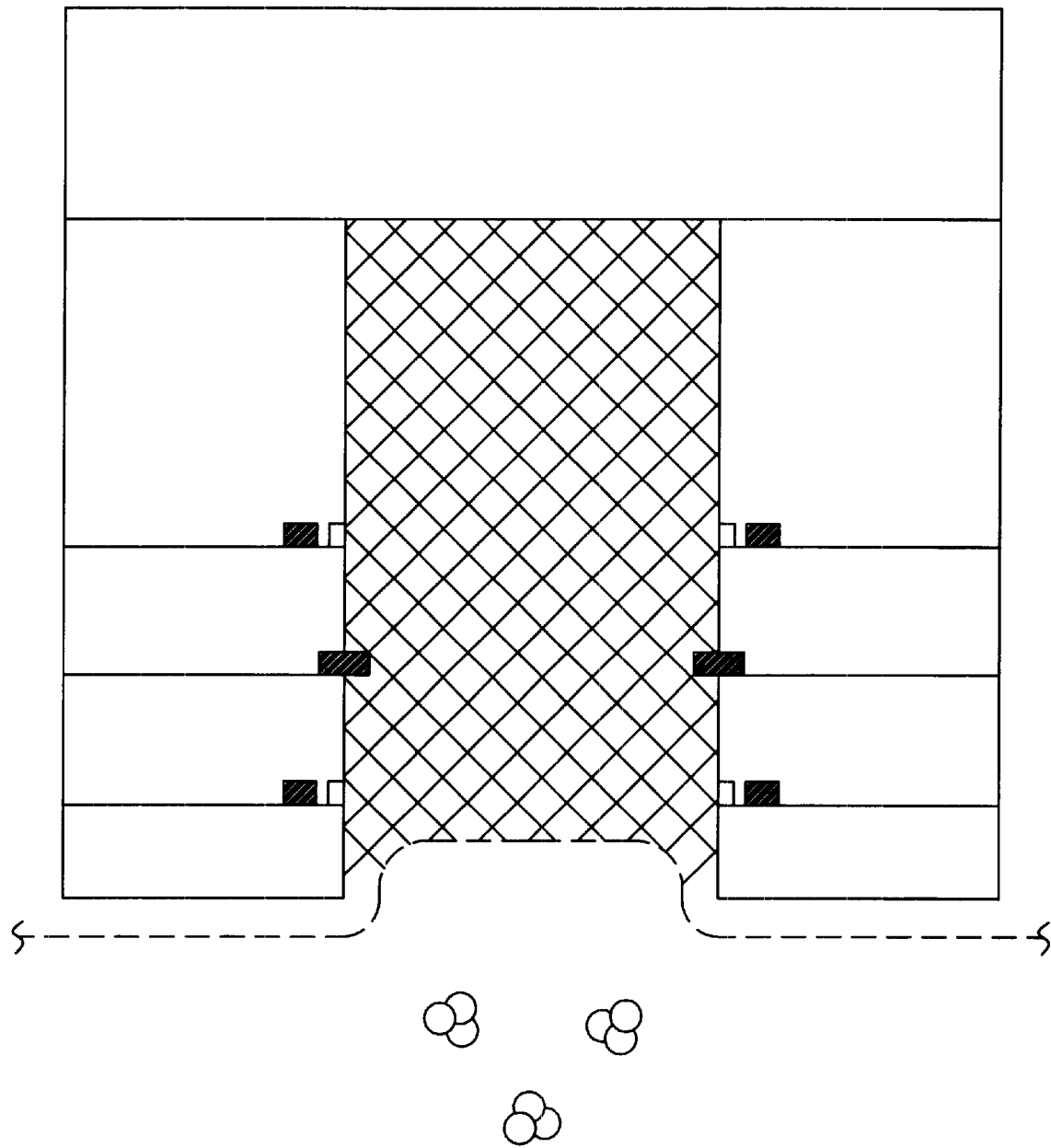
FIG. 29 shows the operation of a sensing reservoir in accordance with one embodiment of the present invention.
Figure 30:
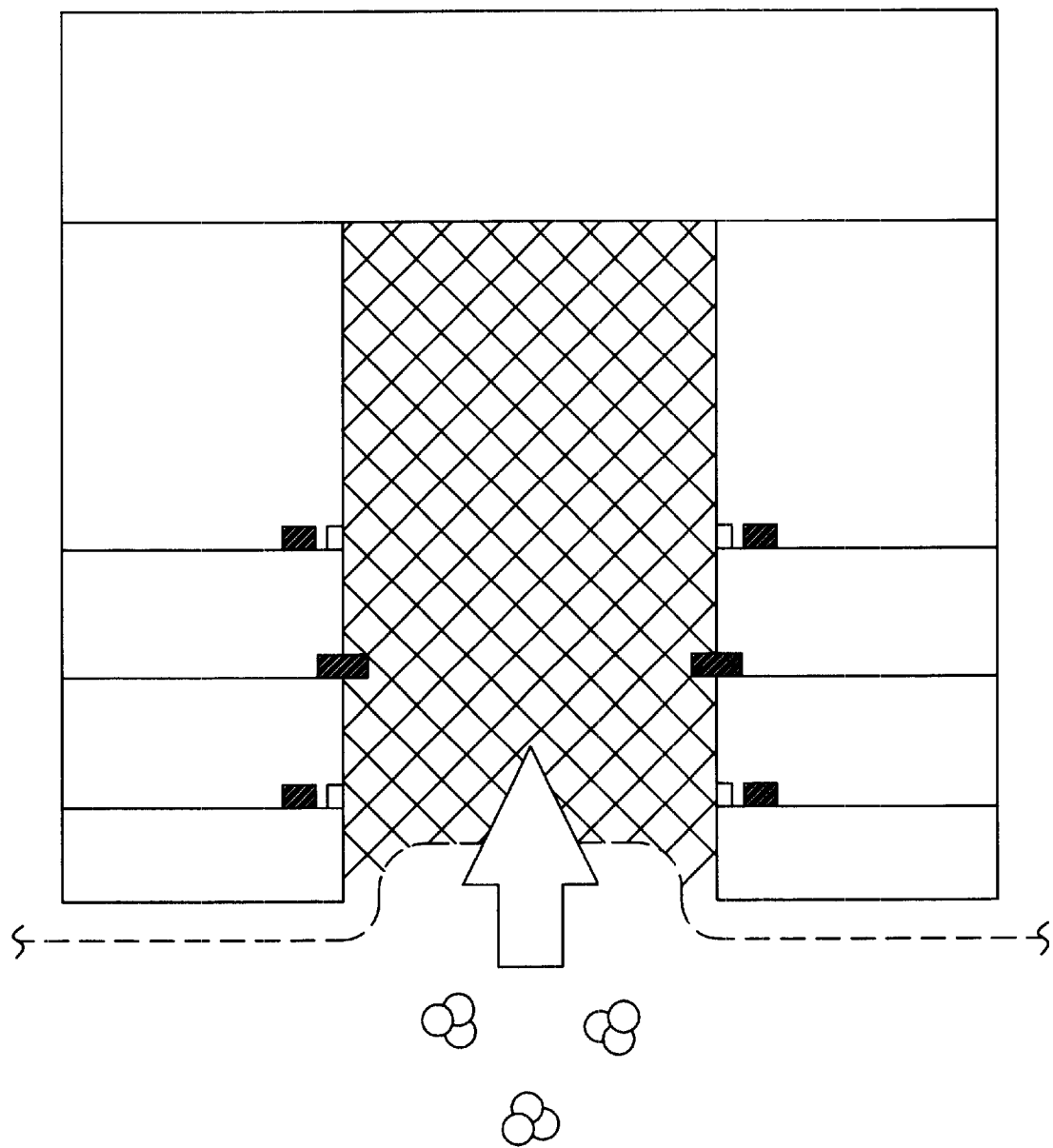
FIG. 30 shows the operation of a sensing reservoir in accordance with one embodiment of the present invention.

FIG. 29 shows the dual stage-sensing reservoir 26b after opening the reservoir cap 27j. FIG. 30 show the semipermeable membrane 27h permitting passage of select interstitial fluids 27i while restricting the mixture 28b from escaping the volume 28a. As interstitial fluids 27i move across the semi-permeable membrane 27h, the fluids 27i come in contact with the reconstituted sensing elements 28b.

Figure 31:
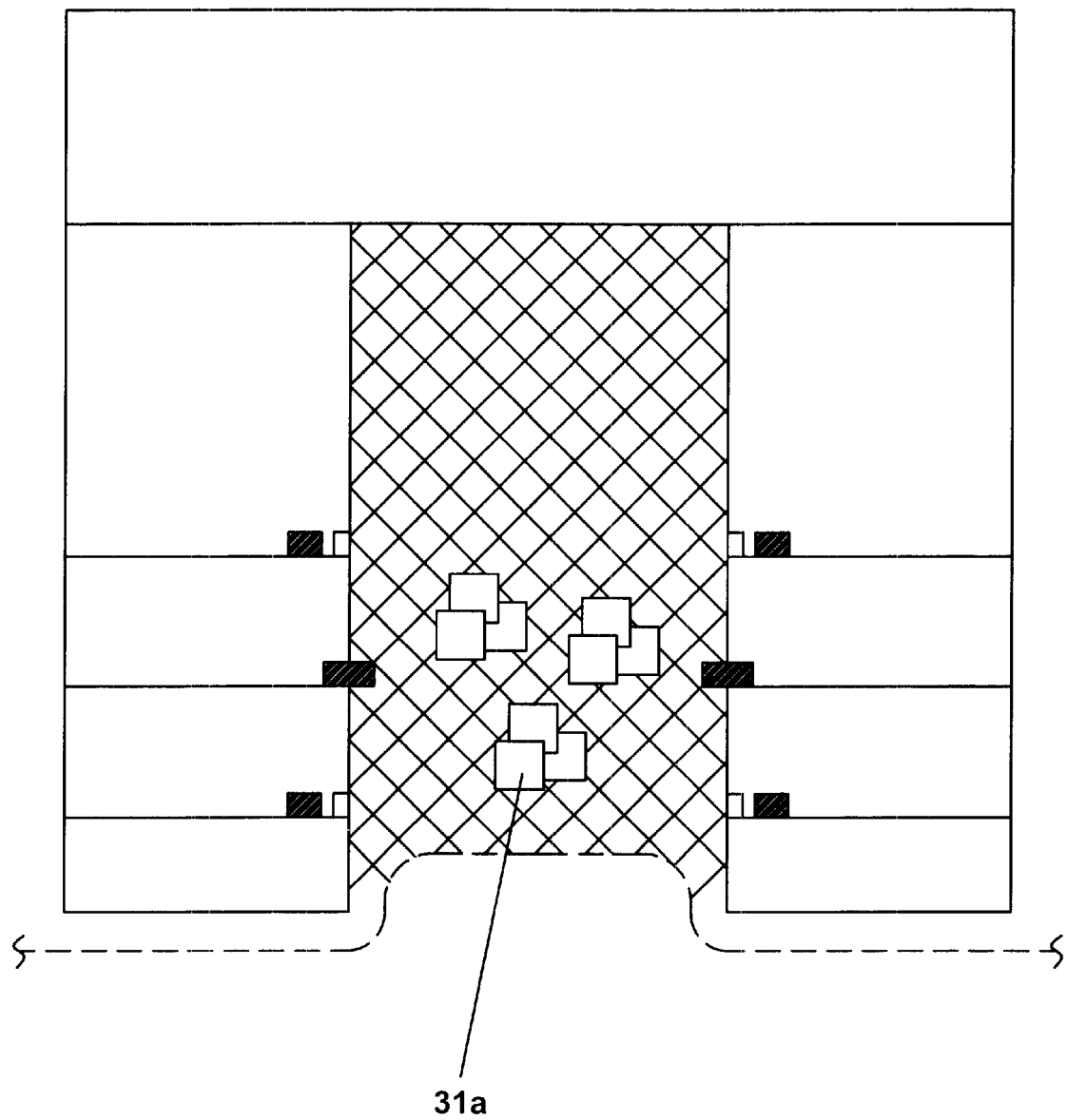
FIG. 31 shows the operation of a sensing reservoir in accordance with one embodiment of the present invention.

FIG. 31 shows the dual stage-sensing reservoir during enzymatic reaction. The select interstitial fluids 27i enzymatically react with the reconstituted sensing elements 28b and generate a signal 31a. The signal 31a is detected by the sensing electrodes 27e and carried to a processor.

A preferred embodiment of FIGS. 25 to 31 utilizes binding proteins in the development of reagentless optical biosensors (1–3)[Salins, 2000]. Specifically, the preferred embodiment uses, but is not limited to, the protein glucose galactose binding protein (GBP). Glucose induces a hinge motion in GBP, and the resulting protein conformational change constitutes the basis of the sensor development. Labeling this protein with a fluorescent probe allows for the monitoring of this change without the addition of any external reagents or substrates. In order to obtain maximal signal versus background fluorescence, the fluorescent probe is attached to a single site, such as but not limited to a unique cysteine, and is at a position where maximum conformational change occurs. Similarly, an electroactive probe could be attached to the same site if electrochemical detection is desired. In the latter case, redox potential changes caused by the change in conformation induced by the binding of glucose to the protein could be monitored by electrochemical means. To detect the electrical signal, the electroactive probe needs to be in electronic contact with the sensing electrode 27e. An example of redox labels, which have been immobilized separately to both on cysteine molecules of a protein as well as on a polymer surface are ferrocene derivatives.

In the preferred embodiment, labeled GBP will be stored dry (lyophilized) in the first stage 27a and a buffer will be placed in the second stage 27c. Any mediators needed for the sensing reaction to occur can also be stored dry in the first stage 27a. The sensing target analyte, in the preferred embodiment, is biological glucose present in the interstitial fluid 27i. At pre-determined periods of time when sensing of glucose is deemed necessary, the reservoir partition 27f between the first stage 27a and second stage 27c will be opened and the dry labeled GBP and the buffer will come in contact. Mixing of the dry sensing reagent, labeled GBP, with the buffer will reconstitute the labeled GBP to its active form.

At this point, in the case of employing electrochemical detection a baseline reading can be obtained by probing the electroactive probe in the GBP in the absence of glucose. After this has been recorded, then a potential will be applied to open the reservoir cap 27j that separates the second stage 27c from the membrane 27h placed surrounding the device and separating it from the interstitial fluid 27i. This will allow for the diffusion of biological glucose to the second stage 27c where it will bind to the labeled GBP and give rise to a signal. A shift in the redox potential of the redox probe on GBP upon binding to glucose will be measured potentiometrically using the sensing electrodes 27e present in the second stage 27c. The signal obtained will be transmitted to a microprocessor. A differential technique will be employed in which the signal ratio obtained between the biological glucose binding to GBP and the non-binding GBP (baseline reading) are monitored. The electrochemical version of the preferred embodiment will be equipped with a telemetric receiver. The electrodes implanted in the patient will be linked to an implanted telemetric transmitter.

A clear advantage of using the device in the sensing mode is related to the minimization of invasive calibration. In order to minimize frequent invasive calibration of the sensors, non-invasive calibration of the sensors can be achieved. Since the proposed embodiment can incorporate a dry reagent that will prolong the lifetime of the sensor, a reduction in calibration frequency can be achieved.

EXAMPLE 2

Drug Delivery

Figure 32:
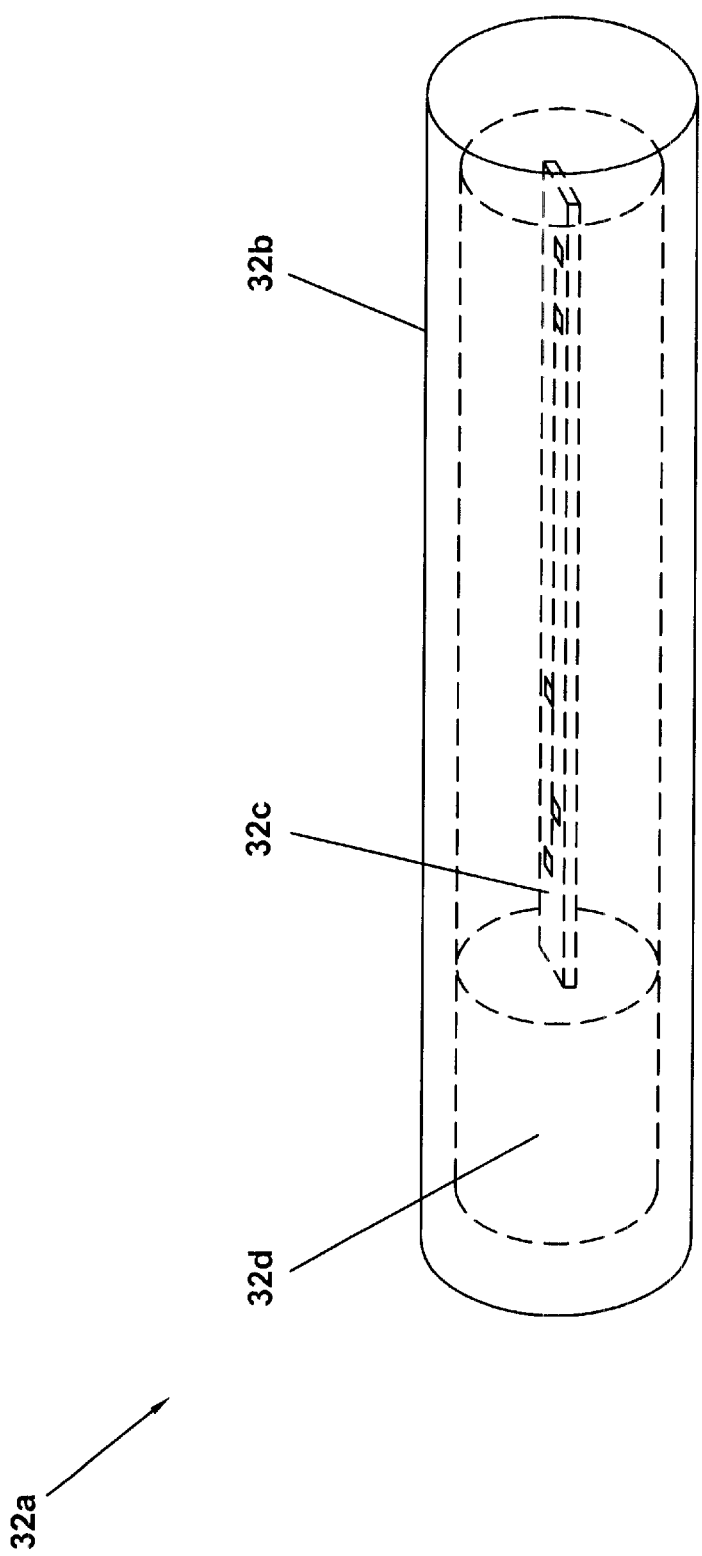
FIG. 32 shows a micro-machined drug delivery device in accordance with one embodiment of the present invention.

With respect to FIG. 32, a micro-machined drug delivery device 32a of the present invention is depicted. The micro-machined drug delivery device 32a comprises a battery 32d, control circuitry 25c and an array of drug delivery reservoirs 32b. In this embodiment the drug delivery reservoirs are positioned about the periphery of the device 32a.

Figure 33:
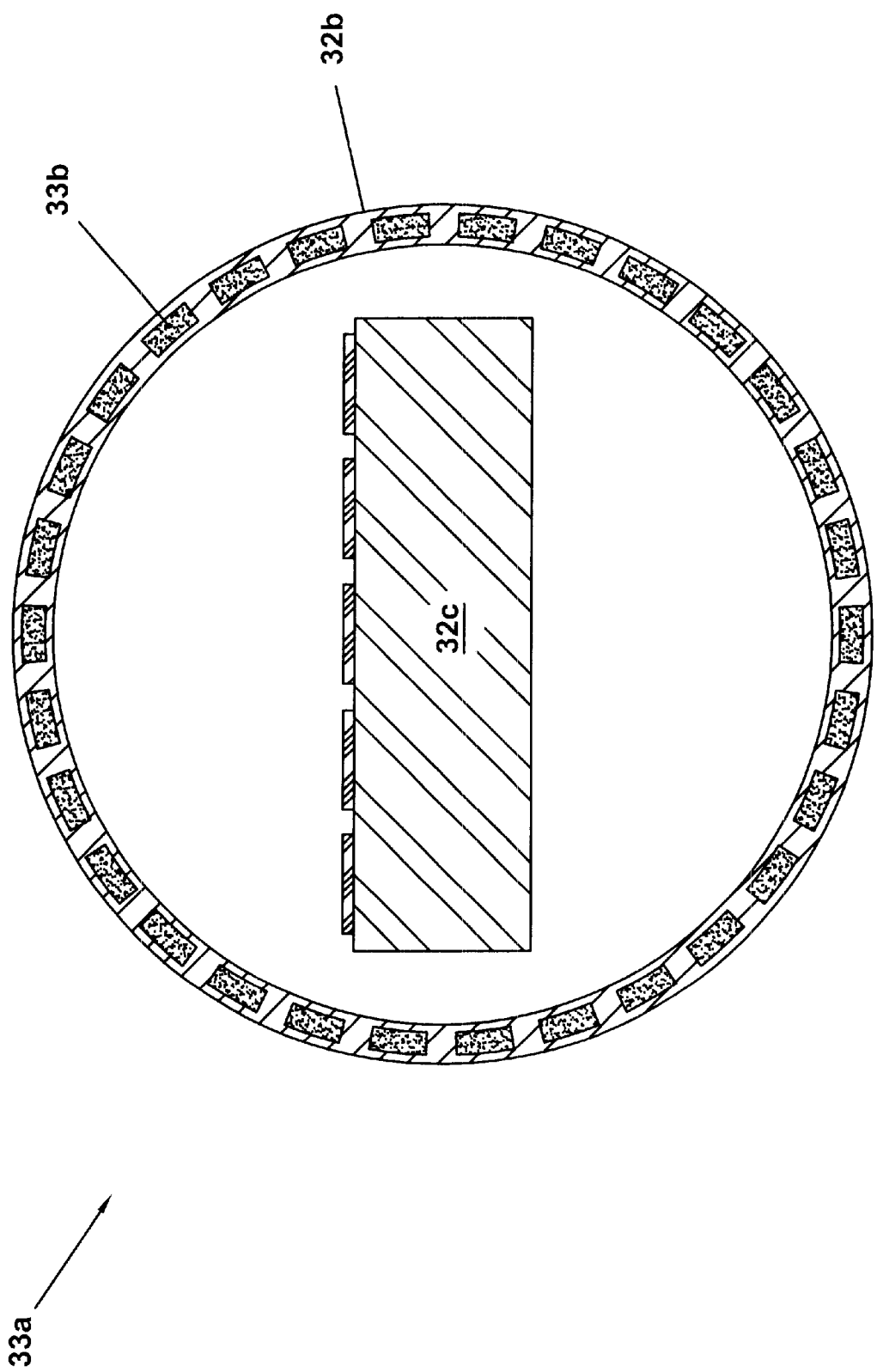
FIG. 33 shows a cross section of the device depicted in FIG. 32.

FIG. 33 shows a cross section of the micro-machined drug delivery device depicted in FIG. 32. The cross section 33a depicts the positioning of the drug delivery reservoirs array 32b about the periphery of the device. The drug delivery array 32b is comprised of individual drug delivery reservoirs 33b.

Figure 34:
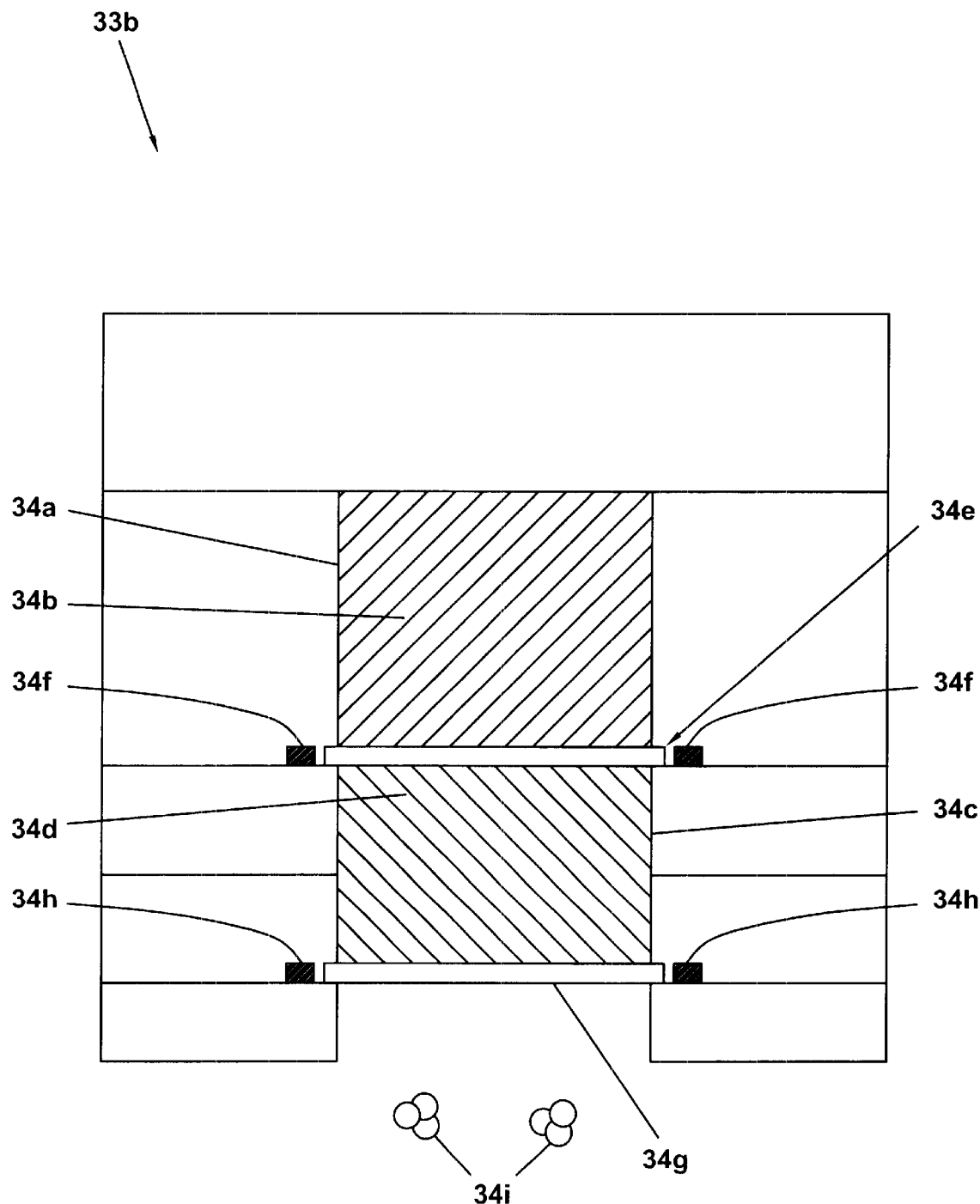
FIG. 34 shows the initial state of a drug delivery reservoir in accordance with one embodiment of the present invention.

FIG. 34 shows the initial state a dual stage drug delivery reservoir 33b in a drug delivery device of the present invention. The dual stage-drug delivery reservoir has a first stage 34a which holds drugs 34b. The device has a second stage 34c which contains drugs 34d. The first stage 34a and the second stage 34c are separated by a reservoir partition 34e. The reservoir partition 34e is in electrical communication with electrical contacts 34f. Applying a voltage via the electrical contacts 34f disintegrates the reservoir partition 34e. The disintegration of the reservoir partition 34e shall be referred to as opening. A reservoir cap 34g separates the second stage 34c from the interstitial fluids 34i of the patient's body. The reservoir cap 34g is in electrical communication with electrical contacts 34h.

Figure 35:
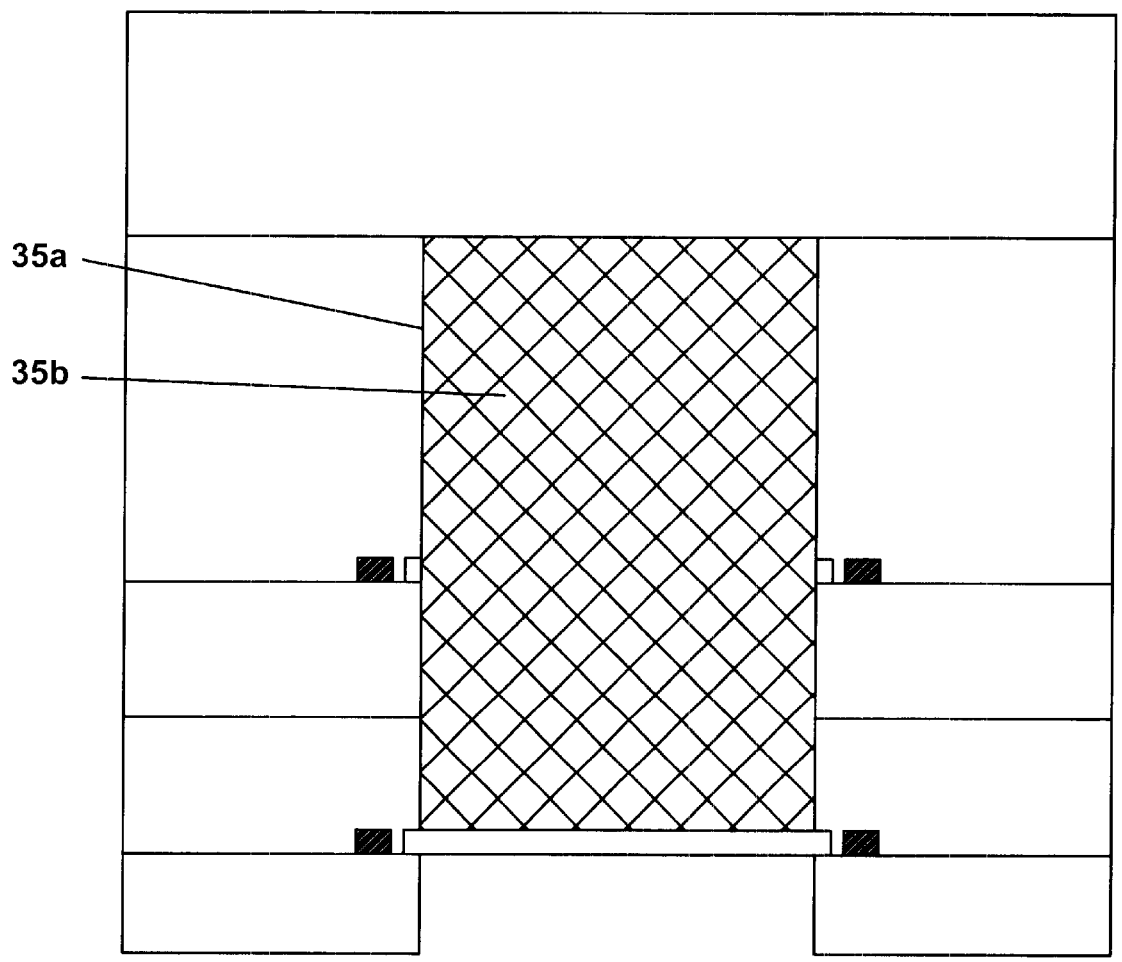
FIG. 35 shows the operation of a drug delivery reservoir in accordance with one embodiment of the present invention.

FIG. 35 shows the dual stage drug delivery reservoir after opening the reservoir partition. The first stage 34a and the second stage 34c combine to form a volume 35a. The volume 35a is now filled with a mixture 35b of the contents of the first stage 34a and the contents of the second stage 34c. The mixture 35b could be an active chemical in a buffer, a drug, a reagent.

Figure 36:
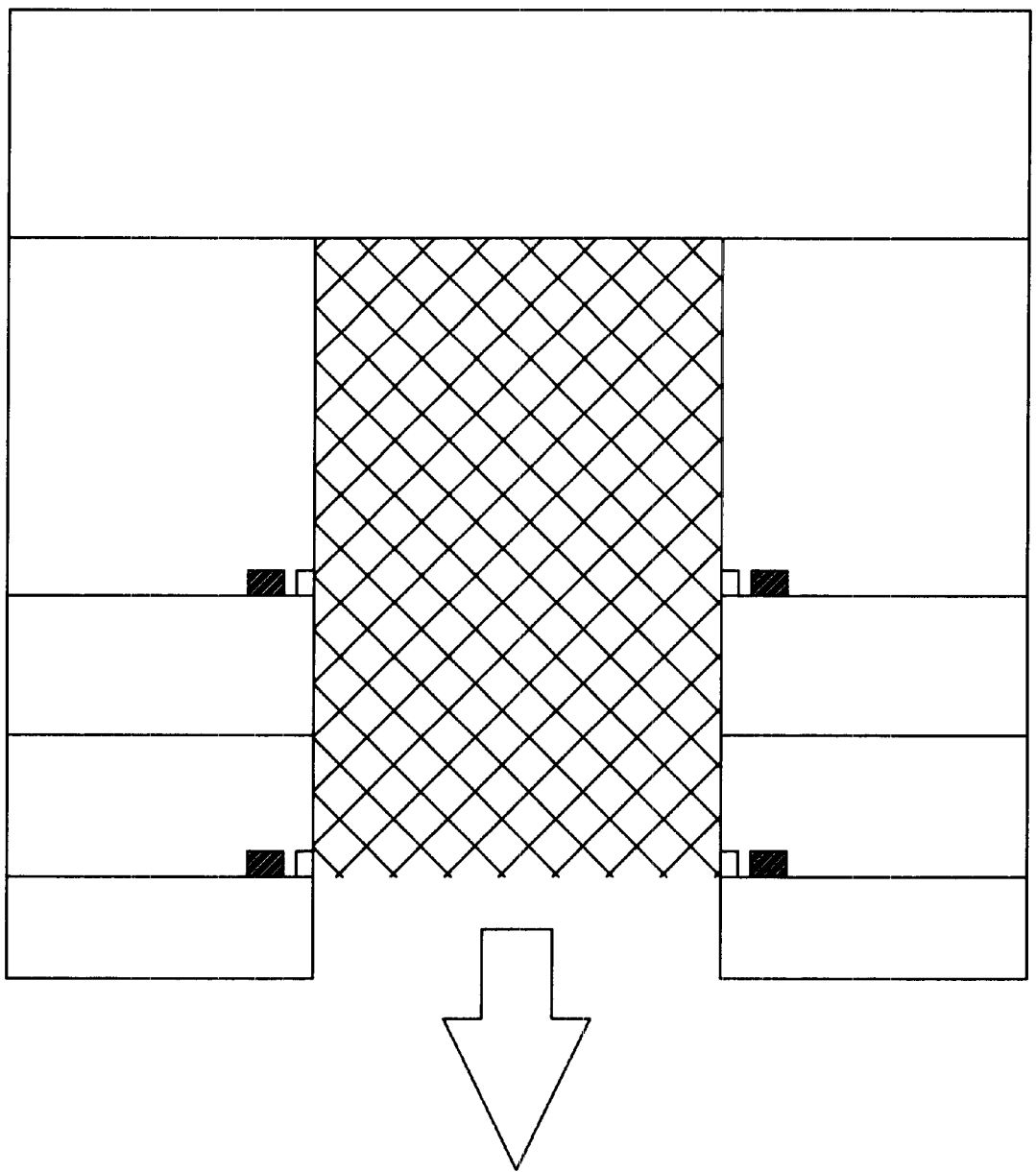
FIG. 36 shows the operation of a drug delivery reservoir in accordance with one embodiment of the present invention.

FIG. 36 shows the dual stage reservoir after opening the reservoir cap 34g. The mixture 35b is free to leave the dual stage reservoir and mix with the interstitial fluids 34i surrounding the micro-machined drug delivery device thereby delivering to the patient a dosage of the mixture 35b.

In a preferred embodiment, a drug that needs to be delivered in response to the levels of biological glucose measured by the sensing device, will be stored dry in a second set of micro-machined dual stage reservoirs 43a, 34c. As in the case of the sensing, the dry (lyophilized) drug plus any adjuvants, stabilizers, etc. needed to prolong its shelf-life or enhance its delivery properties in the body, will be stored in the first stage 34a. The second stage 34c will contain a reconstitution liquid, such as but not limited to buffers or saline solution. Once the measurement of biological glucose has been performed and recorded, the microprocessor will determine how many of the drug delivery chambers need to be opened to release the amount of drug that the patient needs at the particular time. When delivery of drug is needed, the reservoir partition 34e between the first stage 34a and second stage 34c will be opened by applying a potential. This will allow for the drug plus any other reagent present in the first stage 34a to be mixed with the solution present in the second stage 34c. After reconstitution of the dry drug has occurred, the reservoir cap 34g will be opened and the solubilized drug, such as, but not limited to pharmaceuticals, insulin, buffers, biological reagents, cofactors, catalysts, emulsions and surfactants, will start to diffuse through the membrane to the interstitial fluid 34i of the patient. In this preferred embodiment, the delivery device is suitable for the delivery of labile drugs.

EXAMPLE 3

Sensor and Drug Delivery

Figure 37:
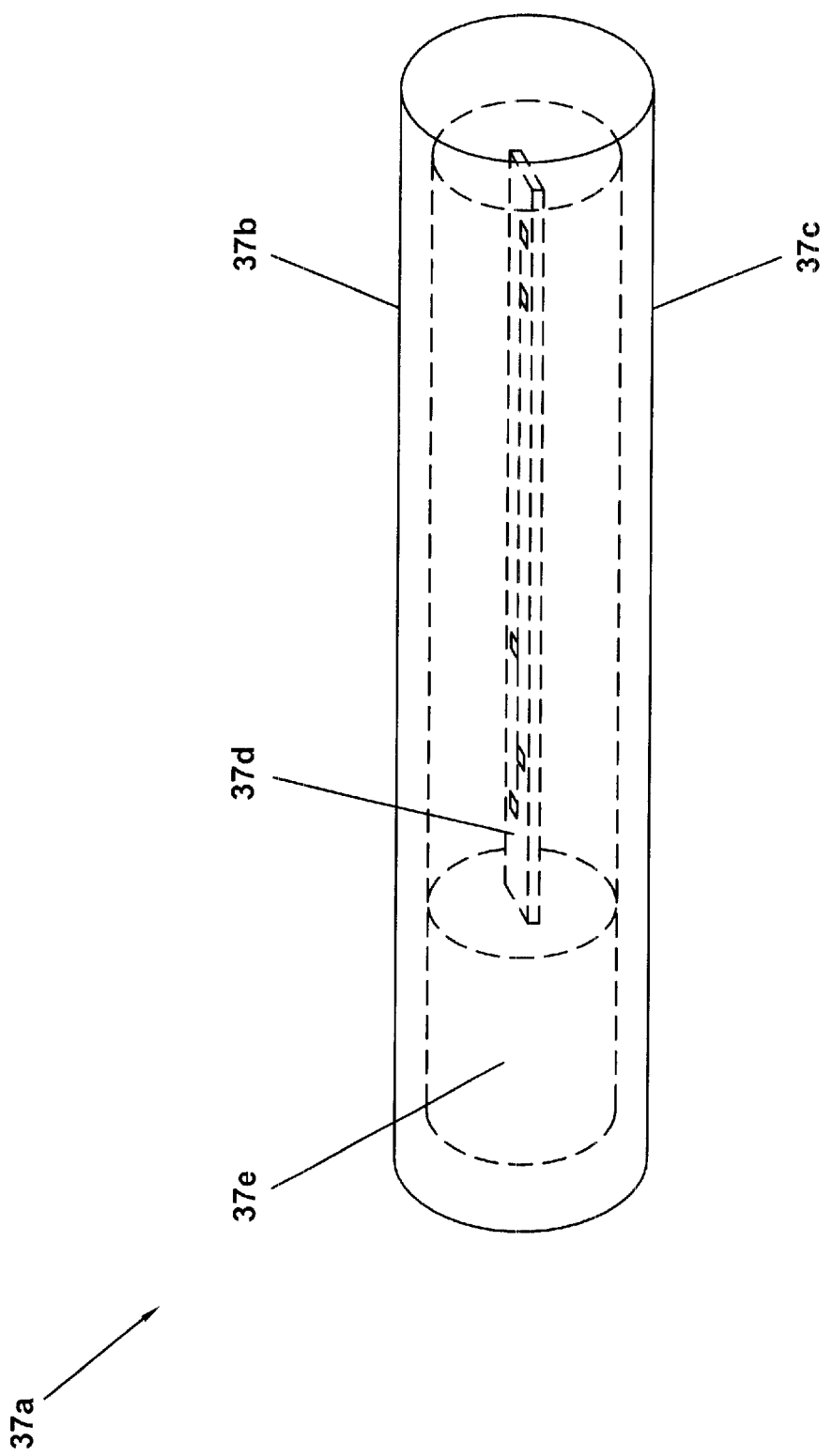
FIG. 37 shows a micro-machined drug delivery and sensing device in accordance with one embodiment of the present invention.

With respect to FIG. 37, a micro-machined drug delivery and sensor device 37a of the present invention is depicted. The micro-machined drug delivery device 37a comprises a battery 37e, control circuitry 37d, an array of drug delivery reservoirs 37b and an array of sensing reservoirs 37c. In this embodiment, the drug delivery reservoirs are positioned about one half of the periphery of the device 37a and the sensing reservoirs are positioned on the remaining half. It should be noted that the actual configuration of the two types of reservoirs on the device are a matter of design choice and should not affect performance in any regard.

Figure 38:
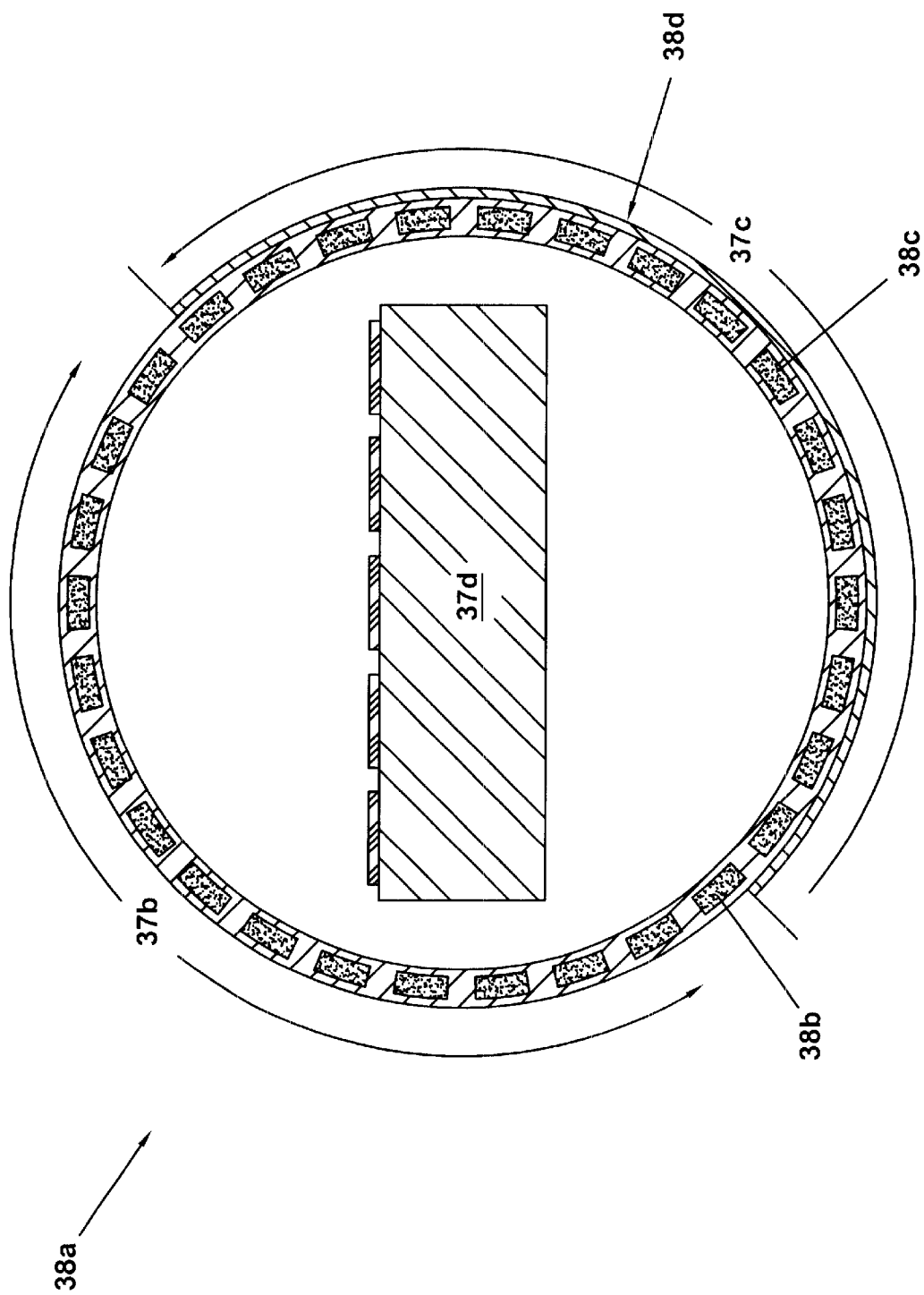
FIG. 38 shows a cross section of the device shown in FIG. 37.

FIG. 38 shows a cross section of one of the micro-machined drug delivery and sensing device depicted in FIG. 37. The cross section 38a depicts the positioning of the drug delivery reservoirs 38b, the sensing reservoirs 38c and the semi-permeable membrane covering the sensing reservoirs 38c.

The operation of the two types of reservoirs has been described in detail above. The control circuitry 37d of the micro-machined drug delivery and sensing device may be adapted to receive a signal from a sensing reservoir 38c and release a drug from a drug delivery reservoir 38b in response thereof.

While the invention has been described in connection with what is presently considered to be the most practical and preferred embodiments, it is to be understood that the invention is not to be limited to the disclosed embodiment, but on the contrary, is intended to cover various modifications and equivalent arrangements included within the spirit and scope of the appended claims, which are incorporated herein by reference.

References

1. Wilson, G. and Y. Hu, Enzyme-based biosensors for in vivo measurements. Chem. Rev., 2000. 100(7): p. 2693–2704.
2. Bowyer, J. R., et al., Energy Res. Abstr., 1991: p. 30.
3. Xie, S. L., E. Wilkins, and P. Atanasov, Sens. Actuators, 1994.17(2): p. 133–42.
4. Madou, M. J. and M. Tierney. 1994: Micro-electrochemical valves and methods, U.S. Pat. No. 5,368,704.
5. GlaxoWellcome, I., www.qlaxowellcome.com.
6. United Therapeutics Corporation S-1 filing. Securities and Exchange Commission: EDGAR, 1999 (April).
7. Badesch, D. E. A., Continuous intravenous epoprostenol for pulmonary hypertension due to the scleroderma spectrum of disease. Ann. Intern. Med., 2000. 132(6): p. 425–434.
8. Dollery, C. T., Ther. Drugs. 1998.
9. Hooper, M. M., M. D., et al., A comparison of the acute hemodynamic effects of inhaled nitric oxide and aerosolized iloprost in primary pulmonary hypertension. American College of Cardiology, 2000. 35(1): p.176–182.
10. Ensor, C. M., et al., Cloning and sequence analysis of the cDNA for human placental AND(+)-dependent 15-hydroxyprostaglandin dehydrogenase. J. Biol. Chem., 1990. 265(25): p.14888–91.
11. Ensor, C. M. and H. H. Tai, Bacterial expression and site-directed mutagenesis of two critical residues (tyrosine-151 and lysine-155) of human placental AND (+)-dependent 15-hydroxyprostaglandin dehydrogenase. Biochim. Biophys. Acta, 1994. 1208(1): p. 151–6.
12. Ensor, C. M., H. Zhang, and H. H. Tai, Purification, cDNA cloning and expression of 15-oxoprostaglandin 13-reductase from pig lung. Biochem. J., 1998. 330(Pt 1): p. 103–8.
13. Drug delivery showing strength in wake of drug efficacy efforts. Chemical Market Reporter, 1997. 252 (September): p. 10.
14. Drug delivery development proliferation. Medical & Healthcare Marketplace Guide, 1997 (January).
15. Drug delivery market faces increased consolidation. Chemical Market Reporter, 1998 (November).
16. Drug delivery systems: polymers expected to dominate world market by 1996. Gazeta Mercantil.
17. Drug delivery changing times. Med. Ad. News, 1999. 18 (August): p. 8.

What is claimed is:

1. A micro-machined drug delivery and biosensing device, for sensing a concentration of a chemical in a patient and administering drugs comprising:
   a. a substrate;
   b. at least one drug delivery reservoir in said substrate, each said drug delivery reservoir having a first stage containing molecules and a second stage containing molecules, each said drug delivery reservoir further having a reservoir partition positioned between and separating said first stage and said second stage, each said reservoir having a reservoir cap positioned over said molecules in said second stage; and
   c. at least one sensing reservoir in said substrate, each said sensing reservoir having a first stage containing molecules and a second stage containing molecules, said second stage of each said sensing reservoir having a pair of sensing electrodes and a reservoir cap positioned over said molecules in each said second stage, each said sensing reservoir further having a reservoir partition separating said first stage from said second stage.

2. The micro-machined drug delivery and biosensing device according to claim 1, wherein at least one said reservoir partition permits said molecules in a said first stage to diffuse through said reservoir partition to a said second stage.

3. The micro-machined drug delivery and biosensing device according to claim 1, wherein at least one said reservoir partition is disintegrated to release said molecules in a said first stage into a said second stage.

4. The micro-machined drug delivery and biosensing device according to claim 1, wherein at least one said reservoir cap permits molecules to diffuse through said reservoir cap so as to release said molecules from said micro-machined drug delivery and biosensing device.

5. The micro-machined drug delivery and biosensing device according to claim 1, wherein at least one said reservoir cap is disintegrated to release said molecules from said micro-machined drug delivery and biosensing device.

6. The micro-machined drug delivery and biosensing device according to claim 1, wherein said molecules in at least one said first stage are a first reactant.

7. The micro-machined drug delivery and biosensing device according to claim 1, wherein said molecules in at least one said second stage are a second reactant.

8. The micro-machined drug delivery and biosensing device according to claim 1, wherein said molecules in a said first stage react with said molecules in a said second stage to form an active drug.

9. The micro-machined drug delivery and biosensing device according to claim 1, wherein said molecules in at least one said first stage is a first active drug.

10. The micro-machined drug delivery and biosensing device according to claim 1, wherein said molecules in at least one said first stage are labile.

11. The micro-machined drug delivery and biosensing device according to claim 1, wherein said molecules in at least one said first stage is a buffer.

12. The micro-machined drug delivery and biosensing device according to claim 1, wherein said molecules in at least one said second stage is a second active drug.

13. The micro-machined drug delivery and biosensing device according to claim 1, wherein said molecules in at least one said second stage are labile.

14. The micro-machined drug delivery and biosensing device according to claim 1, wherein said molecules in at least one said second stage is a buffer.

15. The micro-machined drug delivery and biosensing device according to claim 1, further comprising control circuitry in electrical communication with at least one said reservoir cap, said control circuitry adapted to provide a signal to disintegrate said at least one said reservoir cap.

16. The micro-machined drug delivery and biosensing device according to claim 1, further comprising control circuitry in electrical communication with at least one said reservoir partition, said control circuitry capable of providing a signal to disintegrate said at least one said reservoir partition.

17. The micro-machined drug delivery and biosensing device according to claim 1, further comprising control circuitry capable of sending a signal to a receiver.

18. The micro-machined drug delivery and biosensing device according to claim 1, further comprising control circuitry capable of receiving a signal from a transmitter.

19. The micro-machined drug delivery and biosensing device according to claim 1, further comprising a battery.

20. The micro-machined drug delivery and biosensing device according to claim 1, further comprising a semi-permeable membrane that covers at least one said reservoir cap, said semi-permeable membrane adapted to selectively permit fluids to enter said reservoir, said semi-permeable membrane further adapted to selectively prevent molecules from leaving said reservoir.

21. The micro-machined drug delivery and biosensing device according to claim 1, wherein at least one said reservoir partition is disintegrated to release said molecules in a said first stage into a said second stage to form a sensing element.

22. A method for sensing a concentration of a chemical in a patient's body fluids comprising:

a. inserting a micro-machined sensing device into said patient, said micro-machine sensing device comprising:
   i. a substrate;
   ii. at least one reservoir in said substrate, said reservoir having a first stage containing molecules and a second stage containing molecules;
   iii. a pair of sensing electrodes in said second stage of said reservoir, said sensing electrodes in electrical communication with control circuitry;
   iv. a reservoir cap positioned on each said reservoir over said second molecules in said second stage; and
   v. a reservoir partition separating said first stage from said second stage;

b. contacting said molecules in said first stage with said molecules in said second stage so as to form a sensing element by disintegrating said reservoir partition, said first stage and said second stage combining to form a volume;

c. permitting body fluid to enter said volume where said body fluid reacts with said sensing element to produce a signal detected by said sensing electrodes; and d. sending said detected signal to control circuitry.

23. A method for sensing a concentration of a chemical in a patient's body fluids and releasing drugs into the patient's body, comprising:

a. inserting a micro-machined drug delivery and sensing device into said patient, said micro-machine sensing device comprising:
   i. a substrate;
   ii. at least one drug delivery reservoir in said substrate, each said drug delivery reservoir having a first stage containing molecules and a second stage containing molecules, each said drug delivery reservoir having a reservoir partition positioned between and separating said first and said second stage, each said reservoir having a reservoir cap positioned over said molecules in said second stage;
   iii. at least one sensing reservoir in said substrate, said reservoir having a first stage containing molecules and a second stage containing molecules, a pair of sensing electrodes in said second stage of each said reservoir, said sensing electrodes in electrical communication with control circuitry, a reservoir cap positioned on each said reservoir over said second molecules in said second stage, a reservoir partition separating said first stage from said second stage; and b. contacting said molecules in said first stage of said sensing reservoir with said molecules in said second stage of said sensing reservoir so as to form a sensing element by disintegrating said reservoir partition, said first stage and said second stage of said sensing reservoir combining to form a volume;

c. permitting body fluid to enter said volume where said body fluid reacts with said sensing element to produce a signal detected by said sensing electrodes;

d. sending said detected signal to control circuitry, said control circuitry sending a signal to at least one drug release reservoir in response to said detected signal received by said control circuitry;

e. contacting said molecules in said first stage of said drug release reservoir with said molecules in said second stage of said drug release reservoir so as to form a mixture; and f. releasing said mixture from said micro-machined drug delivery system into said patient.

* * * * *

UNITED STATES PATENT AND TRADEMARK OFFICE
CERTIFICATE OF CORRECTION

PATENT NO. : 6,663,615 B1
DATED : December 16, 2003
INVENTOR(S) : Madou et al.

It is certified that error appears in the above-identified patent and that said Letters Patent is hereby corrected as shown below:

Column 12,
Line 4, please delete "www.qlaxowellcome.com" and insert -- glaxowellcome.com --
Line 17, please delete "human placental AND (+)-dependent" and insert -- human placental NAD (+)-dependent --
Line 22, please delete "of human placental AND" and insert -- of human placental NAD --

Signed and Sealed this

Eighth Day of June, 2004

JON W. DUDAS
*Acting Director of the United States Patent and Trademark Office*